US010525146B2

(12) United States Patent
Rajh et al.

(10) Patent No.: US 10,525,146 B2
(45) Date of Patent: Jan. 7, 2020

(54) METAL OXIDE NANOPARTICLE FOR CELL LYSIS

(71) Applicants: Tijana Rajh, Naperville, IL (US); Elena A. Rozhkova, Lemont, IL (US); Harry C. Fry, Lincolnwood, IL (US); Nada Dimitrijevic, Downers Grove, IL (US); Tamara Koritarov, Naperville, IL (US)

(72) Inventors: Tijana Rajh, Naperville, IL (US); Elena A. Rozhkova, Lemont, IL (US); Harry C. Fry, Lincolnwood, IL (US); Nada Dimitrijevic, Downers Grove, IL (US); Tamara Koritarov, Naperville, IL (US); Bartosz Gryzbowski, Evanston, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 16/385,519

(22) Filed: Apr. 16, 2019

(65) Prior Publication Data

US 2019/0240347 A1 Aug. 8, 2019

Related U.S. Application Data

(63) Continuation of application No. 15/554,423, filed as application No. PCT/US2016/025347 on Mar. 31, 2016, now abandoned.

(60) Provisional application No. 62/142,346, filed on Apr. 2, 2015.

(51) Int. Cl.
   *A61K 47/68* (2017.01)
   *A61K 47/69* (2017.01)
   *C12Q 1/66* (2006.01)
   *A61K 49/12* (2006.01)

(52) U.S. Cl.
   CPC ...... *A61K 47/6863* (2017.08); *A61K 47/6923* (2017.08); *A61K 49/12* (2013.01); *C12Q 1/66* (2013.01)

(58) Field of Classification Search
   None
   See application file for complete search history.

(56) References Cited

U.S. PATENT DOCUMENTS

| 6,677,606 B1 | 1/2004 | Rajh et al. |
| 2003/0087338 A1 | 5/2003 | Messersmith et al. |
| 2007/0007512 A1 | 1/2007 | Dimitrijevic et al. |
| 2008/0226562 A1 | 9/2008 | Groves et al. |
| 2012/0028270 A1 | 2/2012 | Geddes |

FOREIGN PATENT DOCUMENTS

CN 103435829 A 12/2013

OTHER PUBLICATIONS

Allen & Cullis, "Drug delivery systems: Entering the mainstream," Science 303(5665), pp. 1818-1822 (2004).
Allen, et al., "Intracellular binding of wheat-germ agglutinin by golgi complexes, phagosomes, and lysosomes of paramecium-multimicronucleatum," Journal of Histochemistry & Cytochemistry 37(2), pp. 195-202 (1989).
Augulis & Zigmantas, "Two-dimensional electronic spectroscopy with double modulation lock-in detection: Enhancement of sensitivity and noise resistance," Optics Express 19(14), pp. 13126-13133 (2011).
Becher & Holland, "Genetically Engineered Models Have Advantages over Xenografts for Preclinical Studies," Cancer Research 66(7), pp. 3355-3358 (2006).
Chazotte, "Labeling Membrane Glycoproteins or Glycolipids with Fluorescent Wheat Germ Agglutinin," Cold Spring Harbor Protocols, pp. 570-572 (2011).
De La Garza, et al., "Surface states of titanium dioxide nanoparticles modified with enediol ligands," The Journal of Physical Chemistry B 110(2), pp. 680-686 (2006).
Dimitrijevic, et al., "Dynamics of localized charges in dopamine-modified tio2 and their effect on the formation of reactive oxygen species," Journal of the American Chemical Society 131(8), pp. 2893-2899 (2009).
Dreaden, et al., "The golden age: Gold nanoparticles for biomedicine," Chemical Society Reviews 41, pp. 2740-2779 (2012).
Drennan, et al., "Development of DNA dumbbell as a molecular wire," Biophysical Journal 86(1), p. 596A (2004).
Elmore, et al., "Apoptosis: A review of programmed cell death," Toxicologic Pathology 35(4), pp. 495-516 (2007).
Elmouelhi & Yarema, "Building on What Nature Gave Us Engineering Cell Glycosylation Pathways," Biotechnology and Bioengineering, pp. 37-74 (2008).
Elvira, et al., "Targeting neural stem cells with titanium dioxide nanoparticles coupled to specific monoclonal antibodies," Journal of Biomaterials Applications 26(8), pp. 1069-1089 (2011).
Endres, et al., "DNA-TiO2 Nanoconjugates Labeled with Magnetic Resonance Contrast Agents," Journal of the American Chemical Society 129(51), pp. 15760-15761 (2007).
Genoud, et al., "The Protein Phosphatase 7 Regulates Phytochrome Signaling in *Arabidopsis*," PLoS One 3(7), e2699, 10 pages (2008).

(Continued)

*Primary Examiner* — Robert M Kelly
(74) *Attorney, Agent, or Firm* — Foley & Lardner LLP

(57) ABSTRACT

A nanostructure comprises a MOX NP and a bidentate ligand on a surface of the MOX NP. A cancer recognition molecule is covalent coupled to the surface of the MOX NP via the bidentate ligand. A biocatalyst is also coupled to the surface of the MOX nanoparticle via the bidentate ligand. The cancer recognition molecule includes a structure configured to selectively recognize a corresponding antigen on a surface of a cancer cell and bind to the antigen. The biocatalyst is structured to selectively catalyze the oxidation of a light emitting compound to produce photons. The photons transform the MOX NPs into an excited state such that the MOX NPs generate reactive oxygen species (ROS) in the vicinity of the cancer cells in the excited state. The reactive oxygen species lyse or cause apoptosis in the cancer cells in situ. The biocatalyst includes luciferase and the light emitting compound includes luciferin.

17 Claims, 23 Drawing Sheets

(56) References Cited

OTHER PUBLICATIONS

International Search Report and Written Opinion issued in parent application PCT/US2016/025347, dated Jun. 27, 2016, 9 pages.
Kobatake, et al., "Bioluminescent Immunoassay with a Protein A-Luciferase Fusion Protein," Analytical Biochemistry 208(2), pp. 300-305 (1993).
Koritarov, "Photodynamic therapy using luciferase nanoconjugate as a treatment for colon cancer," Boston University, 97 pages (2014).
Lavan, et al., "Small-scale systems for in vivo drug delivery," Nature Biotechnology 21, pp. 1184-1191 (2003).
Lee & Kopelman, "Polymeric Nanoparticles for Photodynamic Therapy," Biomedical Nanotechnology: Methods in Molecular Biology (Methods and Protocols) 726, (2011).
Lee, et al., "Multifunctional nanoparticles for multimodal imaging and theragnosis," Chemical Society Reviews 41, pp. 2656-2672 (2012).
Li, "A targeted approach to cancer imaging and therapy," Nature Materials 13, pp. 110-115 (2014).
Liu, et al., "Hybrid TiO2 nanoparticles: an approach for developing site specific DNA cleavage," Colloidal Quantum Dots for Biomedical Applications 6096, 60960F, 10 pages (2006).
Longmire, et al., "Clearance properties of nano-sized particles and molecules as imaging agents: considerations and caveats," Nanomedicine 3(5), 703-717 (2008).
Lyons, et al., "The Generation of a Conditional Reporter That Enables Bioluminescence Imaging of Cre/IoxP-Dependent Tumorigenesis in Mice," Cancer Research 63(21), pp. 7042-7046 (2003).
Maurer-Spurej, et al., "Factors influencing uptake and retention of amino-containing drugs in large unilamellar vesicles exhibiting transmembrane pH gradients," Biochimica et Biophysica Acta (BBA)—Biomembranes 1416(1-2), pp. 1-10 (1999).
Mills, et al., "Extranuclear apoptosis: The role of the cytoplasm in the execution phase," Journal of Cell Biology 146(4), pp. 703-707 (1999).
Mura, et al., "Stimuli-responsive nanocarriers for drug delivery," Nature Materials 12, pp. 991-1003 (2013).
Nagano, et al., "Distinct cell surface proteome profiling by biotin labeling and glycoprotein capturing," Journal of Proteomics 74(10), pp. 1985-1993 (2011).
O'Brien, et al,. "A human colon cancer cell capable of initiating tumour growth in immunodeficient mice," Nature 445, pp. 106-110 (2007).
Oropesa-Avila, et al., "Stabilization of apoptotic cells: Generation of zombie cells," Cell Death & Disease 5, e1369, 13 pages (2014).
Park, et al., "Stabilin-1 mediates phosphatidylserine-dependent clearance of cell corpses in alternatively activated macrophages," Journal of Cell Science 122, pp. 3365-3373 (2009).
Paunesku, et al., "Biology of TiO2-oligonucleotide nanocomposites," Nature Materials 2, pp. 343-346 (2003).
Pellegatti, et al., "Increased level of extracellular atp at tumor sites: In vivo imaging with plasma membrane luciferase," PLoS One 3(7), e2599, 9 pages (2008).
Petros & Desimone, "Strategies in the design of nanoparticles for therapeutic applications," Nature Reviews Drug Discovery 9, pp. 615-627 (2010).
Rajh, et al., "Improving Optical and Charge Separation Properties of Nanocrystalline TiO2 by Surface Modification with Vitamin C," The Journal of Physical Chemistry B 102(18), pp. 3515-3519 (1999).
Rajh, et al., "Surface Restructuring of Nanoparticles: An Efficient Route for Ligand-Metal Oxide Crosstalk," The Journal of Physical Chemistry B 106(41), pp. 10543-10552 (2002).
Rajh, et al., "Titanium dioxide in the service of the biomedical revolution," Chemical Reviews 114(19), pp. 10177-10216 (2014).
Rego & Batista, "Quantum dynamics simulations of interfacial electron transfer in sensitized tio2 semiconductors," Journal of the American Chemical Society 125(26), pp. 7989-7997 (2003).
Kolhkova, et al., "A high-perrormance nanobio photocatalyst for targeted brain cancer tnerapy," Nano Letters 9(9), pp. 3337-3342 (2009).
Scott, et al., "Antibody therapy of cancer," Nature Reviews Cancer 12, pp. 278-287 (2012).
Shang, et al., "Engineered nanoparticles interacting with cells: size matters," Journal of Nanobiotechnology 12(5), 11 pages (2014).
Soares, et al., "Glycophthalocyanines as photosensitizers for triggering mitotic: Catastrophe and apoptosis on cancer cells," Chemical Research in Toxicology 25(4), pp. 940-951 (2012).
Stagg & Smyth, "Extracellular adenosine triphosphate and adenosine in cancer," Oncogene 29, pp. 5346-5358 (2010).
Tachan, et al., "The TiO2-Catechol Complex: Coupling Type II Sensitization with Efficient Catalysis of Water Oxidation," Advanced Energy Materials 4(6), 1301249, 7 pages (2014).
Thorne, et al., "Illuminating Insights into Firefly Luciferase and Other Bioluminescent Reporters Used in Chemical Biology," Chemistry & Biology 17(6), pp. 646-657 (2010).
Tomlinson, et al., "Human colon cancer cells express multiple glycoprotein ligands for e-selectin," International Journal of Oncology 16(2), pp. 347-400 (2000).
Virostko, et al., "Bioluminescence Imaging in Mouse Models Quantifies β Cell Mass in the Pancreas and After Islet Transplantation," Molecular Imaging and Biology 12(1), pp. 42-53 (2010).
Wang, et al., "Label-free measuring and mapping of binding kinetics of membrane proteins in single living cells," Nature Chemistry 4, pp. 846-853 (2012).
Xu, et al,. "Photokilling cancer cells using highly cell-specific antibody-tio2 bioconjugates and electroporation," Biochemistry 71(2), pp. 217-222 (2007).
Zidek, et al., "Electron relaxation in the cdse quantum dot—zno composite: Prospects for photovoltaic applications," Scientific Reports 4, 7244, 8 pages (2014).

METAL OXIDE NANOPARTICLE FOR CELL LYSIS

CROSS-REFERENCE TO RELATED APPLICATIONS

The present application is a continuation of U.S. Non-Provisional application Ser. No. 15/554,423, filed Aug. 29, 2017, now abandoned, which is a U.S. national stage entry of International Patent Application No. PCT/US2016/025347 filed Mar. 31, 2014, which claims priority to and benefit of U.S. Provisional Patent Application No. 62/142,346, filed Apr. 2, 2015, the entire disclosures of which are incorporated herein by reference.

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to nanoparticles for lysing cancer cells in vivo.

BACKGROUND

Recent progress in advanced medical therapies is focused on single cell level resolution. Such technologies hold promise to reduce off-target effects by directing therapeutic agents exclusively to localized diseased tissue. Several factors are important for the cell-targeted therapies among which prevention of premature release of the toxic remedies is one of the most important ones. Several drug delivery systems activated by heat, magnetic fields, ultrasound, or light are being explored. The other attractive approach to localized therapies is the use of molecules that are produced by the disease itself as a trigger activating the therapy.

New therapies for cancer treatment are focused on targeted drug delivery of a therapeutic to a target site where cancer cells are located within the body of a patient. For example, many naturally derived, recombinant or synthetic ligands (e.g., antibodies, antibody fragments, aptamers, etc.) can specifically bind to corresponding antigens expressed on a surface (i.e., a cell membrane) of specific cancer cells. However, conventional drugs have numerous side effects which can still be present in spite of targeted drug delivery. Other approaches have used carriers that rely on pH change across the liposome bilayer or pathophysiological abnormalities of vascular system in the cancerous tissues (EPR effect) to passively accumulate and retain the drug in the vicinity of diseased targets.

SUMMARY

Embodiments described herein relate generally relate to metal oxide (MOX) nanoparticles (NPs) for lysing cancer cells in vivo, and in particular to semi-conductor MOX NPs that include a cancer recognition antibody and a biocatalyst coupled to a surface of the MOX NPs via a bidentate ligand. In various embodiments, the MOX NPs are configured to lyse cancer cells in situ in the presence of a light emitting compound and adenosine triphosphate (ATP).

In some embodiments, a nanostructure includes a MOX NP and a bidentate ligand disposed on a surface of the MOX NP. A cancer recognition molecule is covalent coupled to the surface of the MOX NP via the bidentate ligand. A biocatalyst is also coupled to the surface of the MOX nanoparticle via the bidentate ligand. The cancer recognition molecule comprises a structure configured to selectively recognize a corresponding antigen on a surface of a cancer cell and bind to the antigen. Furthermore, the biocatalyst is structured to selectively catalyze the oxidation of a light emitting compound to produce photons. The photons transform the MOX NPs into an excited state such that the MOX NPs generate reactive oxygen species (ROS) in the vicinity of the cancer cells in the excited state. The reactive oxygen species lyse or cause the cancer cells to undergo apoptosis in situ. In one embodiment, the biocatalyst includes luciferase and the light emitting compound includes luciferin.

In another embodiment, a method of treating cancer using a nanostructure which includes a MOX NP having a cancer recognition molecule and a biocatalyst coupled to a surface of the MOX NP via a bidentate ligand, includes injecting a plurality of nanostructures into a blood stream of a patient having cancer cells which produce ATP. The nanostructures are incubated within the blood stream of the patient for a first predetermined time to selectively bind the plurality of MOX NPs to the cancer cells via the cancer recognition molecule. A light emitting compound is injected into the blood stream of the patient. The light emitting compound is incubated in the blood stream of the patient for a second predetermined time to allow the light emitting compound to be transported to the nanostructures selectively bound on the cancer cells. Oxidation of the light emitting compound is catalyzed by the biocatalyst in the presence of the ATP to produce photons in proximity of the cancer cells to excite the MOX NPs. The MOX NPs generate ROS in proximity of the cancer cells. The cancer cells are at least one of lysed or undergo apoptosis in situ by interaction with the ROS. In certain embodiments, the biocatalyst includes luciferase and the light emitting compound includes luciferin.

In some embodiments, a method of formulating a cancer treating composition comprises incubating a biocatalyst with a bidentate linker in a buffer solution at a predetermined pH. The incubating causes the biocatalyst to covalently couple to the bidentate linker, thereby forming a biocatalyst coupled bidentate linker. The biocatalyst coupled bidentate linker is incubated with metal oxide (MOX) nanoparticles so as to covalently couple the MOX nanoparticles to the bidentate linker and, thereby the biocatalyst. Separately, a cancer recognition molecule is incubated with the bidentate linker so as to covalently couple the cancer recognition molecule to the bidentate linker, thereby forming a cancer recognition molecule coupled bidentate linker. The cancer recognition molecule coupled bidentate linker is incubated with the MOX nanoparticles coupled to the biocatalyst, the incubating causing the cancer recognition molecule to also be coupled to the MOX nanoparticles via the bidentate linker so as to form the cancer treating composition. The cancer recognition molecule comprises a structure configured to selectively recognize a corresponding antigen on a surface of a cancer cell and bind to the antigen. The biocatalyst is structured to selectively catalyze the oxidation of a light emitting compound to produce photons. The photons transform the MOX nanoparticles into an excited state. The MOX nanoparticles generate reactive oxygen species in the vicinity of the cancer cells in the excited state, which lyse the cancer cells or cause apoptosis in the cancer cells.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 7 panel B is a plot of kinetics of light emission of free luciferase (10 nM) and luciferin (40 μM) in solution, free luciferase and luciferin in the presence of, but not conjugated to, an equimolar concentration of $TiO_2$-DOPAC (10 nM particles), and TiDoL nanoparticles (10 nM) and luciferin (40 μM) in solution; FIG. 7 panel C is a schematic of experimental luciferin induced current measurement setup in conjunction with current (FIG. 7 panel D) generated by the luciferase mediated conversion of luciferin in TiDoL films as a function of ATP concentration, current measurements were performed on the electrodes in a solution of 10 mM MES buffer (pH 6.1) and 5 mM hydroquinone purged with Argon (Ar); FIG. 7 panel E is a plot of bioluminescence emitted by the luciferase-mediated catalysis of luciferin at various concentrations of ATP, minimal bioluminescence is emitted at ATP concentrations found in healthy tissue (low micro-molar levels) for both unconjugated luciferase and luciferase that has been conjugated to $TiO_2$-DOPAC nanoparticles.

FIG. 12 panel G is a 3D image of treated cells stained with MITOSOX® Red for obtaining distribution of superoxide radicals within treated cells.

FIG. 18 panel C includes an optical fluorescence image (left) and a TEM image (right) of young adult mouse colonocyte or colonic epithelial (YAMC) cells treated with TiDoL-C225-Alizarine.

Figure 1:
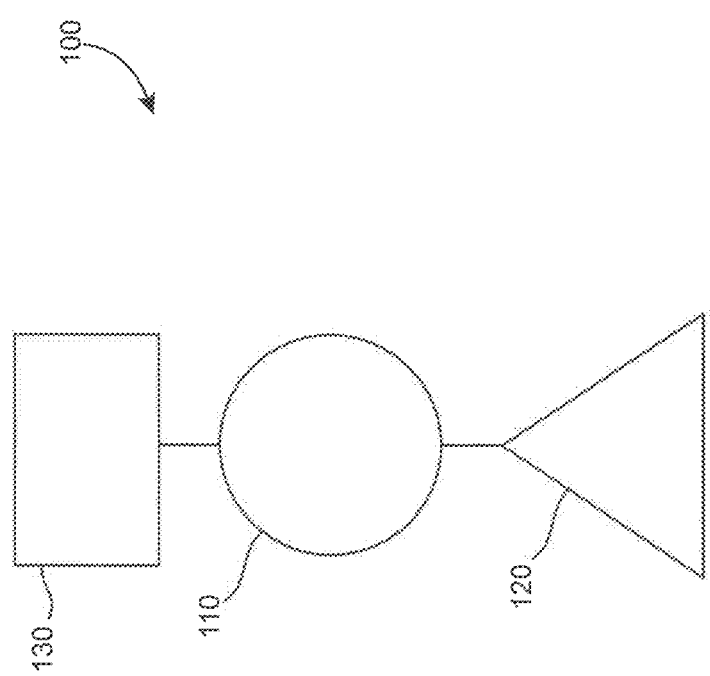
FIG. 1 is an illustration of a nanostructure that includes a MOX NP, and a cancer recognition molecule and a biocatalyst coupled to the MOX NP via a bidentate ligand, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein generally relate to metal oxide (MOX) nanoparticles (NPs) for lysing cancer cells in vivo, and in particular to semi-conductor MOX NPs that include a cancer recognition antibody and a biocatalyst coupled to a surface of the MOX NPs via a bidentate ligand. In various embodiments, the MOX NPs are configured to lyse cancer cells in situ in the presence of a light emitting compound and adenosine triphosphate (ATP).

Embodiments of the nanostructures described herein provide several benefits including, for example: (1) targeted delivery of nanostructures to cancer cell sites in a patient in vivo by simple intravenous delivery; (2) coupling a cancer recognition antibody as well as luciferase to a single MOX NPs, and using ATP produced by cancer cells and intravenously or orally injected luciferin to generate photons in the proximity of MOX NPs which are bound to cancer cells of a patient which may be located deep within the body of a patient; (3) providing cell lysing capabilities by in vivo generation of reactive oxygen species (ROS) by photoexcitation of the MOX NPs in the vicinity of the cancer cells to lyse the cells in situ; and (4) using biocompatible MOX NPs, cancer recognition antibodies and luciferin thereby, minimizing or eliminating side effects commonly associated with chemotherapy and other invasive cancer therapies.

FIG. 1 is an illustration of a nanostructure 100. The nanostructure 100 includes a MOX NP 110, a bidentate ligand (not shown) disposed on a surface of the MOX NP 110, a cancer recognition molecule 120, and a biocatalyst coupled to the surface of the MOX NP 110, via the bidentate ligand.

The MOX NP 110 can include any suitable semi-conductor metal oxide. Suitable materials can include, for example $TiO_2$, $Fe_xO_y$, $CeO_2$, $ZrO_2$, $V_xO_y$, $Mo_xO_y$, $Mn_xO_y$, NiO, $Cu_xO_y$, AgO, ZnO or any other semi-conductor metal oxide, where "x" and "y" represent all suitable proportion of the metal and oxygen in the MOX NP. In some embodiments, the MOX NP 110 can include a hybrid metal/MOX NP. Such hybrid metal/MOX NPs can include, for example, core-shell metal/MOX NPs in which the NP 110 has a metallic core and a MOX shell, dumb-bell shaped hybrid metal/MOX NPs or combinations thereof. Suitable metals which can be used to form the hybrid metal/MOX NPs include, for example, Ag, Au, Pt, Pd, etc.

In one embodiment, the MOX NP can include $TiO_2$. The MOX NP 110 is photoactive. That is, in the presence of a photon source at an appropriate wavelength, the MOX NP 110 is transformed to an excited state, as described in detail herein.

Figure 2:
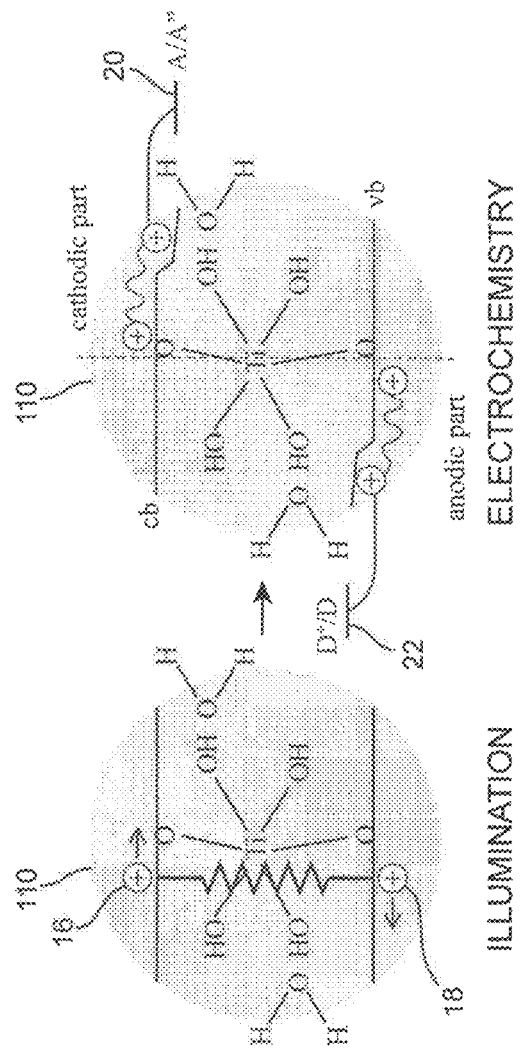
FIG. 2A is a schematic illustration of a MOX NP without illumination.
FIG. 2B shows the MOX NP of FIG. 2A subjected to illumination.
FIG. 2C illustrates redox reactions occurring on a surface of the MOX NP upon illumination.

Expanding further, FIGS. 2A-2C are schematic illustrations of the MOX NP 110 without the bidentate linker, the cancer recognition molecule 120, and the biocatalyst 130. The semi-conductor MOX NP 110 has an energy and structure characterized by a gap between the highest occupied energy level 12 (or valence band) and the lowest 20 unoccupied energy level 14 (or conduction band). For example, in the case of $TiO_2$, the gap is 3.2 e V. A disturbance in the energy level of the electrons in the valence band in the semiconductor is induced via illumination with photons (FIG. 2B).

Figure 3:
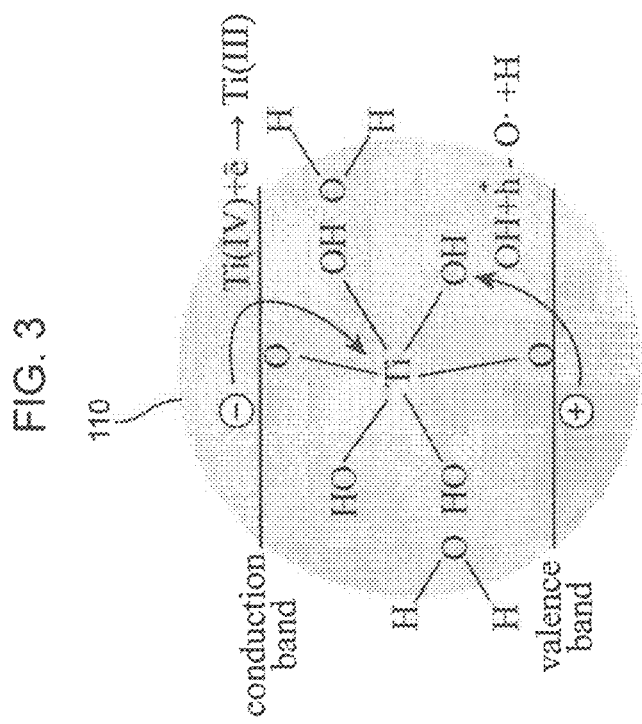
FIG. 3 is a schematic diagram of the fate of photogenerated charge pairs in a $TiO_2$ NP.

Upon illumination with photons having energy greater than the band gap, an electron 16 is excited to the conduction band 14 while in the valence band 12 a positive hole 18 is created. As shown in FIG. 2C, the electrons and holes generated via the illumination can separate and diffuse to the surface of the semiconductor. This surface diffusion allows the diffused electrons and holes to react with redox couples to undergo reduction reactions 20 and oxidation reactions 22, respectively. For example, FIG. 3 shows a $TiO_2$ NP which is excited by photons such that electrons of the $TiO_2$ NP jump from the valence band to the conduction band. The electrons which have been energized to the conduction band of the $TiO_2$ NP, are trapped as reduced metal centers. The electrons facilitate reduction of Ti (IV) to Ti (III). Concomitantly, the holes left in the valence band are trapped as oxygen centered radicals covalently linked to surface titanium atoms.

These oxygen centered radicals and electrons trapped as Ti(III) centers allow the excited MOX NP 110 to undergo a redox reaction with water or oxygen (e.g., the water or oxygen present in cells such as cancer cells or in the extracellular matrix surrounding cells) to produce ROS (e.g., hydroxyl radicals (—OH), hydrogen peroxide ($H_2O_2$), superoxide ($O_2^-$), peroxide ($O_2^{2-}$), etc.). ROS are highly reactive and tend to trigger apoptosis in cells, which eventually leads to cell lysis and death. Thus, the MOX NP 110 can be used for targeting and lysing cancer cells.

As described herein, the MOX NP 110 can include a hybrid metal/MOX NP. The metal (e.g., Au, Ag, etc.) included in such hybrid metal/MOX NPs can enhance electromagnetic field around the MOX, enhance interaction of photons with MOX, and/or enhance charge separation and therefore ROS production of the NP 110.

Generally, the MOX NPs 110 (e.g., $TiO_2$) are sensitive to light at a wavelength of about 400 nm, which is below the visible regime. Coupling of the bidentate ligand to the surface of the MOX NPs shifts the excitation wavelength of the MOX NPs to about 560-600 nm which is in the visible regime. Furthermore, the bidentate ligand can allow covalent coupling of organic molecules, for example, anti-bodies, peptides, enzymes, dyes, aptamers, DNA, or any other molecule to the surface of the MOX NP 110. In some embodiments, the coupling of the organic molecule with the MOX NP 110 can be achieved using 1-ethyl-3-3-dimethylaminopropyl]carbodiimide hydrochloride (EDC) and n-hydroxysuccinimide (NHS) chemistry or variations thereof. In some embodiments, the bidentate ligand can include an enediol ligand such as, for example the bidentate ligand can include dihydroxyl phenyls e.g., 1,2-dihydroxyl phenylamine, 1,2-dihydroxyl phenyl alanine, 1,2-dihydroxyl benzoic acid, 1,2-dihydroxyl glycine, 1,2-dihydroxyl benzyl amine, dopamine, 3,4-dihydroxyphenylacetic acid (DOPAC) and combinations thereof. In particular embodiments, the bidentate ligand includes DOPAC.

Expanding further, the bidentate ligand provides enhanced charge separation of the MOX NP 110. The charge pairs are instantaneously separated into two phases, the holes on the donating organic modifier and the donated electrons in either the conduction band or valence band of the semi-conductor. This causes a red shift in the excitation wavelength of the MOX NP 110 so that the MOX NP 110 is excitable by visible light, as well as allows the excited electron to spend a longer time in the conduction band thereby providing better opportunity for the MOX NP 110 to engage in a redox reaction (e.g., to generate ROS).

Figure 4:
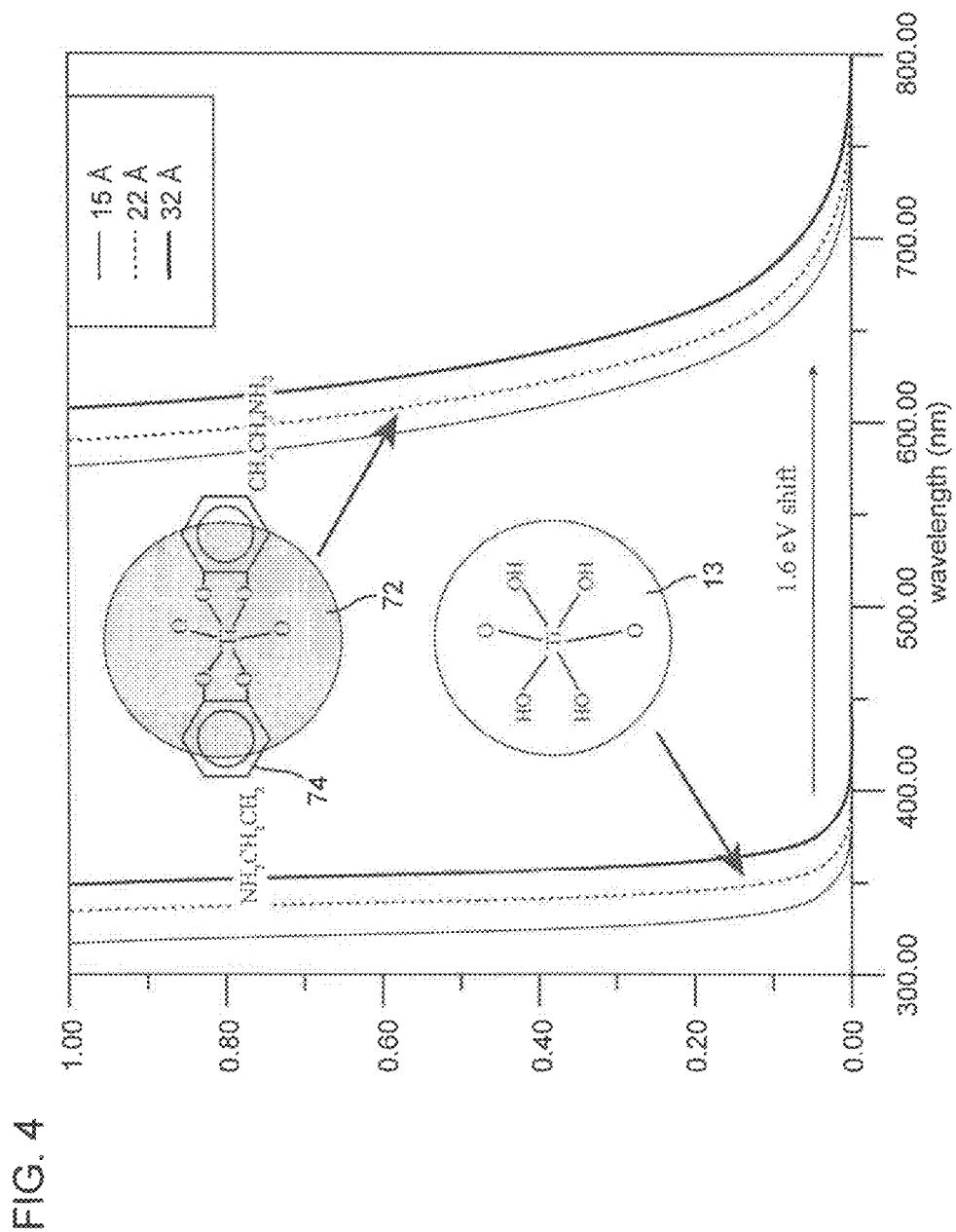
FIG. 4 is a plot of red shift in the excitation wavelength of a $TiO_2$ after coupling the bidentate ligand onto a surface of the $TiO_2$ NP.

For example, as shown FIG. 4, unmodified $TiO_2$ NP 13 exhibits absorbency at approximately 400 nm. However, when a bidentate ligand (such as dopamine 74 or DOPAC) is attached to the particle, the resulting construct 72 exhibits a shift in absorbency to a longer wavelength of approximately 560-600 nm. Bidentate ligands introduce mid gap states that contribute to enhanced density of states in the mid gap region. The absorption in the red region reflects excitation of electrons from the mid gap states localized on bidentate ligands to the conduction band of $TiO_2$ resulting in charge transfer absorption.

Referring again to FIG. 1, the cancer recognition molecule 120 is coupled to the surface of the MOX NP 110 via the bidentate ligand. The cancer recognition molecule can include an antibody (monoclonal, polyclonal, naturally occurring, recombinant or synthetic), antibody fragments (e.g., Fab fragments), peptides, aptamers or any other suitable molecule which can detect a cancer cell. The cancer recognition module 120 is structured to selectively recognize a corresponding antigen on a surface (i.e., a cell membrane) of the cancer cell and bind to the antigen. In this manner, the cancer recognition molecule 120 is used to selectively recognize and bind to the cancer cell to position the MOX NP 110 in proximity of the cancer cell. In some embodiments, the cancer cell can ingest the MOX NP 110 through the cell membrane such that the MOX NP 110 is delivered to the cytoplasm of the cancer cell. Any suitable cancer recognition molecule 120 can be used to target any cancer cell (e.g., colorectal cancer, pancreatic cancer, liver cancer, prostate cancer, stomach cancer, throat cancer, brain cancer, melanoma, A172 human glioblastoma, astrocytoma, IL-13Ra2-positive U251 MG, IL-13Ra2-positive cancer cells or any other cancer for which a selective cancer recognition molecule 120 is available). In a particular embodiment, the cancer recognition molecule 120 includes C225 antibody, C225 Fab fragment or corresponding peptides.

In some embodiments, the cancer recognition molecule 120 can be coupled to the MOX NP 110 via EDC-NHS chemistry via the bidentate ligand. For example, the cancer recognition molecule 120 can include an antibody. In a first step, the cancer recognition molecule 120 (e.g., an antibody) is modified at its carboxylic terminus to contain an ester-moiety. The carboxyl terminus is transformed into a succinimide intermediate via extraction of the hydroxyl moiety. Then, in a nucleophilic substitution reaction, the succinimide group is expelled and its place taken by a basic amino group to form an antibody with an ester terminus. The ester terminus reacts with one or a plurality of bidentate ligands to form antibody linked to the bidentate ligand thereby, coupling the antibody to the surface of the MOX NP 110. In some embodiments, the bidentate ligand can be first reacted with the cancer recognition molecule 120 to form cancer recognition molecule/bidentate ligand complex which can then be coupled to the MOX NP 110 via the bidentate ligand. In other embodiments, the bidentate ligand can be coupled to the surface of the MOX NP 110 before coupling the cancer recognition molecule 120 to the bidentate ligand.

The biocatalyst 130 is also coupled to the MOX NP 110 via the bidentate ligand. For example, the biocatalyst 130 can be coupled to the bidentate ligand and thereby, to the MOX NP 110 using EDC-NHS chemistry as described herein with respect to the cancer recognition molecule 120. The biocatalyst 130 is structured to selectively catalyze the oxidation of a light emitting compound to produce photons. For example, the biocatalyst 130 can include an enzyme structured to selectively recognize and catalyze an oxidation (or reduction) of the light emitting compound to generate photons. The photons generated by the oxidation of the light emitting compound can be in the visible regime i.e., having a wavelength in the range of about 560 nm. The photons generated by the light emitting compound transform the MOX NP 110 into its excited state, as described before herein.

In this manner, the MOX NP 110 can generate ROS as described herein. If the MOX NP 110 is in proximity of the cancer cells, for example bound to the cancer cell via the cancer recognition molecule 120 and the light emitting compound is delivered proximal to the cancer cells (e.g., attached to the cancer cells or positioned within a distance of less than 10 micron, less than 5 microns, less than 1 microns, or less than 500 nanometers of the cancer cells inclusive of all ranges and values therebetween), the photons are generated in the vicinity of cancer cells proximal to the MOX NP 110. Thus, the MOX NP 110 bound to the cancer cells is transformed into the excited state and produces ROS in the vicinity of the cancer cells (or within the cancer cells). The ROS triggers apoptosis in the cancer cells leading to the inactivation and death of the cancer cells.

Any biocatalyst 130 and light emitting compound can be used. In one embodiment, the biocatalyst 130 can include luciferase and the light emitting compound can include luciferin. Luciferase is an enzyme found in fireflies. It catalyzes the oxidation of luciferin in the presence of ATP via the following reactions:

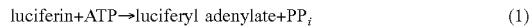

$$\text{luciferin} + \text{ATP} \rightarrow \text{luciferyl adenylate} + \text{PP}_i \quad (1)$$

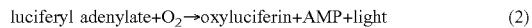

$$\text{luciferyl adenylate} + O_2 \rightarrow \text{oxyluciferin} + \text{AMP} + \text{light} \quad (2)$$

Light is emitted because the reaction forms oxyluciferin in an electronically excited state. The reaction releases a photon of light as oxyluciferin returns to the ground state. The wavelength of the emitted light is about 560 nm which is sufficient to excite the bidentate ligand coupled MOX NP 110. In some embodiments, the nanostructure 100 can be subjected to a magnetic field. The magnetic field may enhance efficiency of luciferin/luciferase luminescence and/or prolong lifetime of charge separated pair due to correlation of radical pairs in magnetic field.

Cancer cells generally produce about 100 times more ATP relative to healthy cells, possible due to the high metabolic demand. Thus, the ATP required in the luciferin reaction catalyzed by luciferase is already present in excess within and/or proximal to the cancer cells. To target the cancer cells, the nanostructure 100 can be delivered to the cancer cells (e.g., injected in a blood stream of a patient or administered orally) where the nanostructure 100 can selectively bind to the cancer cell via the cancer recognition molecule 120, as described above. Luciferin can then be delivered to the proximity of the cancer cells (e.g., injected into a blood stream or administered orally) where the luciferin is oxidized in a reaction catalyzed by the luciferase coupled to the surface of the MOX NP 110 (e.g., TiO$_2$ NP). This produces photons having a wavelength in the visible regime which excites the MOX NP 110 thereby producing ROS in the vicinity of the cancer cells and triggering apoptosis in the cancer cells, as described above.

In some embodiments, the nanostructure 100 can also be used as a nanosensor for detecting cancer. As described herein, the excess ATP surrounding the cancer cells allows the production of luminescence in the vicinity of the nanostructure 100 bound to the cancer cells. This luminescence is expected to be about 100 times higher near the cancer cells than healthy cells, as cancer cells are known to produce at least 100 times more ATP than healthy cells. The luminescence can be viewed using any suitable imaging technique (e.g., magnetic resonance imaging (MM)) to pinpoint the location of the cancer cells within a body of a cancer patient.

Figure 5:
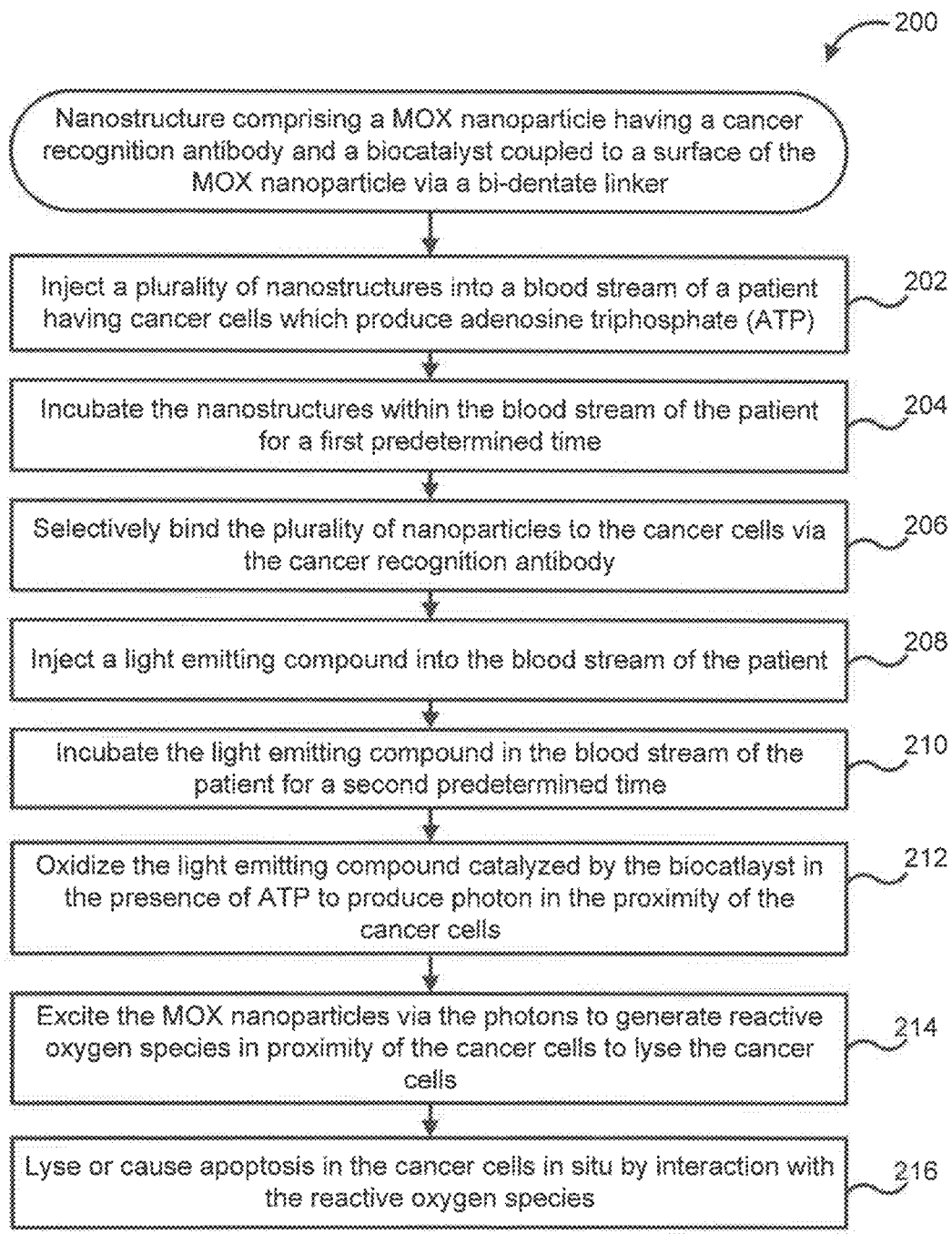
FIG. 5 is a schematic flow diagram of a method of lysing cancer cells in situ using MOX NPs, according to another embodiment.

FIG. 5 is a schematic flow diagram of an exemplary method 200 for treating cancer using a nanostructure including a MOX NP having a cancer recognition molecule and a biocatalyst coupled to a surface of the MOX NP via a bidentate ligand (e.g., the nanostructure 100, or any other nanostructure described herein). In some embodiments, the MOX NP can include TiO$_2$ or any other MOX NP described herein. In particular embodiments, the MOX NP can include a hybrid metal/MOX NP as described herein with respect to the nanostructure 100.

The method includes injecting a plurality of the nanostructures into a blood stream of a patient having cancer cells at 202. The cancer cells produce ATP as described with respect to the nanostructure 100. The cancer cells can be located deep within the body of a patient. Such cancers can include, for example colorectal cancer, pancreatic cancer, liver cancer, prostate cancer, stomach cancer, throat cancer, ovarian cancer, lung cancer (e.g., non-Hodgkin's lymphoma), brain cancer (e.g., A172 human glioblastoma, astroglioma, astrocytoma), melanoma, IL-13Ra2-positive U251 MG, IL-13Ra2-positive cancer cells or any other cancer for which a selective cancer recognition molecule is available.

The nanostructures are incubated within the blood stream of the patient for a first predetermined time at 204. The incubation for the first predetermined time allows the nanostructures to be transported to the cancer site as the blood circulates through the body of the patient.

The plurality of nanoparticles selectively bind to the cancer cells via the cancer recognition molecule at 206. As described before, the cancer recognition molecule (e.g., the cancer recognition molecule 120) can include an antibody structured to recognize and selectively bind to a corresponding antigen expressed on a surface of the target cancer cells. In this manner, the nanostructure can be bound and localized on the cancer cells via the cancer recognition molecule. In particular embodiments, the nanostructure can be ingested into a cytoplasm of the cancer cells as described herein.

A light emitting compound is injected into the blood stream of the patient at 208. In some embodiments, the biocatalyst included in the nanostructure includes luciferase. In such embodiments, the light emitting compound includes luciferin. The light emitting compound is incubated in the blood stream of the patient for a second predetermined time at 210. The incubating for the second predetermined time allows the light emitting compound to be transported to the nanostructures selectively bound on the cancer cells.

The light emitting compound is oxidized in the presence of ATP in a reaction catalyzed by the biocatalyst to produce photons in proximity of the cancer cells at 212. For example, the light emitting compound includes luciferin and the biocatalyst includes luciferase. The luciferase catalyzes the oxidation of luciferin to produce photons in the visible regime, as described herein.

The MOX NPs included in the nanostructure are excited via the photons to generate ROS in proximity of the cancer cells at 214. Thus, photons are produced in the proximity of the nanostructures at the site where the cancer cells are located, which can be deep within the body of the patient. This avoids the use of external light sources which cannot penetrate deep into the human body to deliver the photons to nanostructures targeting cancer cells located deep within the human body. The ROS produced in the vicinity of the cancer cells can trigger apoptosis in the cancer cells or lyse the cancer cells. In this manner, the method 200 can be used for targeted delivery of the nanostructures to the cancer cells in vivo and selectively bind the nanostructures to the cancer cells, and moreover to generate photons in situ to selectively kill the cancer cells in situ.

Since the high amounts of ATP are only produced by the cancerous cells, the low amounts of ATP produced in the vicinity of healthy cells, which is in the sub-micromoles/L range, is insufficient to cause any meaningful oxidation of the luciferin catalyzed by luciferase. Thus, very little or no light is generated in the vicinity of healthy cells limiting the production of ROS to high ATP sites which are in proximity of the cancer cells. In contrast, the amount of ATP around cancer cells is in the 100's of micromoles/L range, that is about 100 times higher than the ATP produced by healthy cells. This amount of ATP can lead to significant oxidation of luciferin catalyzed by the luciferase bound to the MOX NP. In this manner, the MOX NPs only targets the cancer cells with minimal or no damage to the healthy cells surrounding the cancer cells.

In some embodiments, the MOX NP attached to the cancer cells can be exposed to a magnetic field to enhance the charge pair separation and/or efficiency of luciferase/luciferin luminescence. For example, the patient can be positioned in an MRI machine which can provide the magnetic field, or magnets (natural or electromagnetic) can be strategically positioned on the body of the patient such that a magnetic field is produced in the vicinity of the nanostructures attached to the cancer cells within the body of the patient.

In this way the release of toxic reactive species is doubly regulated: (i) by positioning of $TiO_2$ NPs near cancerous cells using the cancer recognition molecule (e.g., cell specific antibodies), and (ii) by the level of ATP production. Even if the small fraction of nanoparticles binds to a non-cancerous cell, the absence or very low concentration of extracellular ATP around healthy cells will prevent light forming cascade in non-cancerous tissues. Efficiency of this approach relies on i) efficiency of self-powering $TiO_2$ nanoparticles to absorb emitted light (about 560 nm) and ii) their ability to integrate both proteins that together mediate site selective light activity (antibodies and luciferase). Furthermore, ROS species generally diffuse only within one micron of the ROS generation site before they are neutralized. This limits the impact radius of the ROS species generated by the nanostructures to within close proximity (e.g., within one micron radius) of the cancer cells, thereby limiting or preventing any adverse impact of the ROS on the adjacent healthy cells.

In some instances, consumption of ATP surrounding the cancer cells during the luciferin oxidation reaction can disrupt cell signaling and other key metabolic processes involved with cancer cells in addition or in parallel to triggering apoptosis in the cancer cells. In such instances, growth and replication of the cancer cells can be stunted such that further spread of the cancer is prevented. In other words, a single therapeutic dose of the nanostructures (e.g., the nanostructure 100) can be used to target and trigger apoptosis in a portion of the cancer cells via ROS mediated oxidative stress. Furthermore, consumption of extracellular ATP around the cancer cells controls and limits growth and replication of any cancer cells which survived the initial therapeutic dose of the nanostructures. These cancer cells can then be targeted by the nanostructures in subsequent rounds of therapy until all the cancer cells are neutralized.

In some embodiments, a protein-A-luciferase chimera can be synthesized ex vivo which is capable of binding to the Fc segment of a cancer recognition antibody. In this manner, MOX NPs 110 covalently linked to monoclonal antibody specific to cancer cells can be associated with the protein-A-luciferase chimera and site selectively delivered to the cancer cells.

In other embodiments, a genetically fused chimera of a cancer specific monoclonal antibody and luciferase can be expressed in *E. coli*, purified and covalently linked to the MOX NPs 110. In still other embodiments, healthy cells surrounding the cancer cells can be transfected with plasma membrane bidentate ligand labeled luciferase and engineered to express bidentate labeled luciferase in the vicinity of cancer cells. In such embodiments, the MOX NPs 110 with only the cancer recognition molecule 120 bound thereto and excluding the luciferase are delivered to the cancer cell site to selectively bind to the cancer cells, as described herein. When luciferin is delivered to the cancer cell site, luciferase expressed by the adjacent healthy cells is present to catalyze the oxidation of luciferin leading to the production of ROS.

EXPERIMENTAL EXAMPLES

Figure 6:
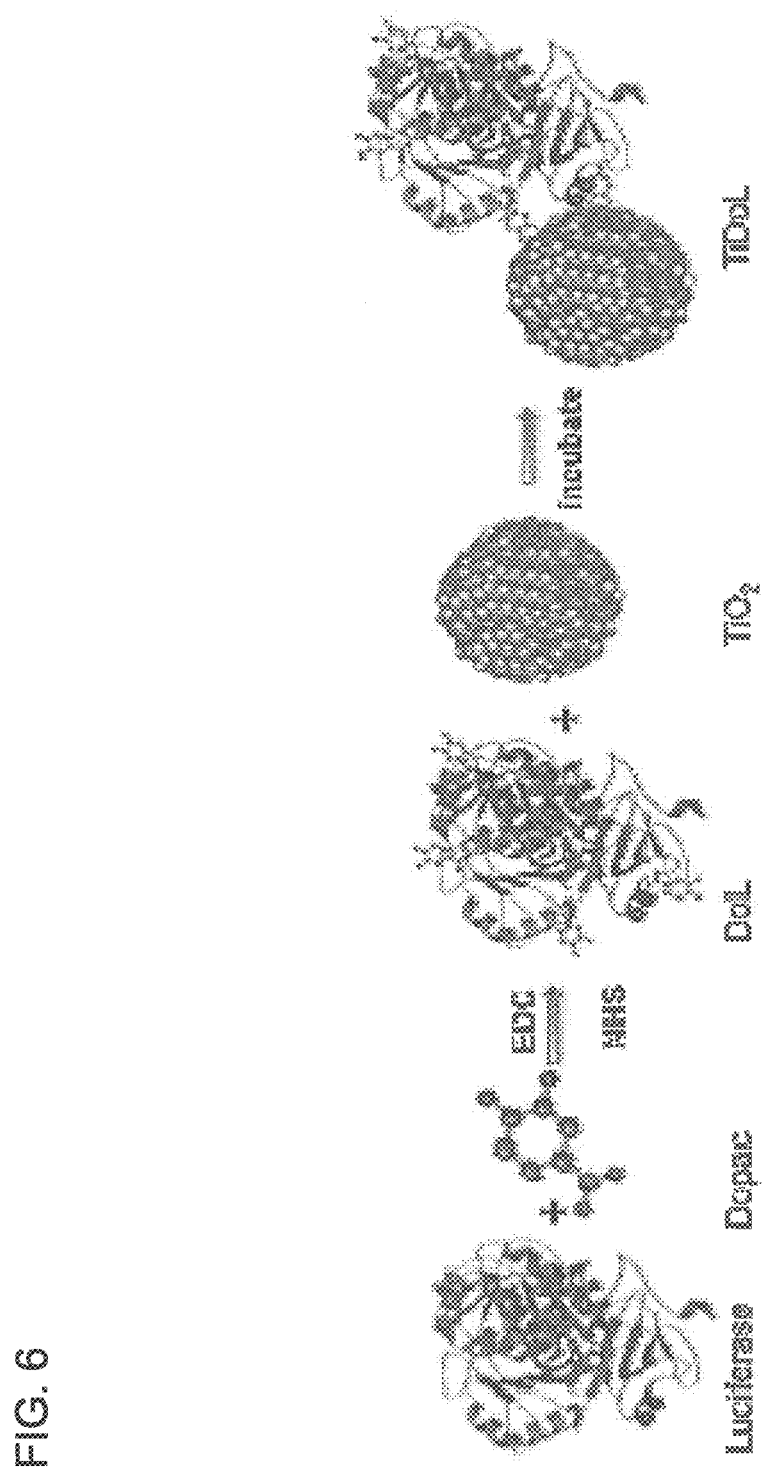
FIG. 6 is a schematic illustration of a method of coupling 3,4-dihydroxyphenylacetic acid (DOPAC) with luciferase to form a complex (DoL), and further coupling the DoL to a surface of a titanium oxide ($TiO_2$) NP via the DOPAC to form a $TiO_2$-DOPAC-luciferase (TiDoL) NP.

FIG. 6 shows a method of synthesizing luciferase-$TiO_2$ NPs (TiDoL NPs). In the first step DOPAC is incubated with luciferase and subsequently reacted using EDC-NHS chemistry at pH 6.8 in PBS buffer. DOPAC labeled Luciferase (DoL) is than incubated with 5 nm $TiO_2$ nanoparticles to result in luciferase covalently linked to $TiO_2$ nanoparticles via conductive linker (TiDoL).

Expanding further, the TiDoL nanostructures were prepared by covalent linking of 10 nM luciferase (*Photinus pyralis* (firefly)) with equimolar particle concentration of 5 nm-$TiO_2$ nanoparticles through DOPAC as shown in FIG. 6. In order to link negatively charged $TiO_2$ nanoparticles (in 10 mM phosphate buffered saline, PBS, pH 7) to luciferin that has an overall negative charge (formal negative charge of −7.0), DOPAC (20 fold excess) was first incubated with luciferin in order to position negatively charged carboxyl group in the positive pockets of luciferin followed by EDS/sulfo-NHS conjugation of DOPAC to amino groups of luciferase. $TiO_2$ NPs were than incubated with (comprehensively washed) DOPAC modified luciferase.

Due to their high degree of surface curvature, bare $TiO_2$ NPs have surface atoms in distorted crystalline environment and under-coordinated geometry. These under-coordinated sites at the surface of small $TiO_2$ NPs exhibit high reactivity toward bidentate coordination with oxygen-containing ligands enabling their seamless coupling to small molecules such as DOPAC. Bidentate binding of DOPAC to under-coordinated sites results in reconstruction of the surface atoms of $TiO_2$ NPs to thermodynamically stable octahedral geometry. This, in turn, introduces new electronic states in the mid gap region of $TiO_2$ NPs that originate from DOPAC HOMO and lead to enhanced optical properties of the NPs in the visible region of the spectrum. As a result, only successful coupling of bare $TiO_2$ NPs to DOPAC modified luciferase will result in the electronic interaction manifested by the appearance of the visible absorption band of TiDoL.

Figure 7:
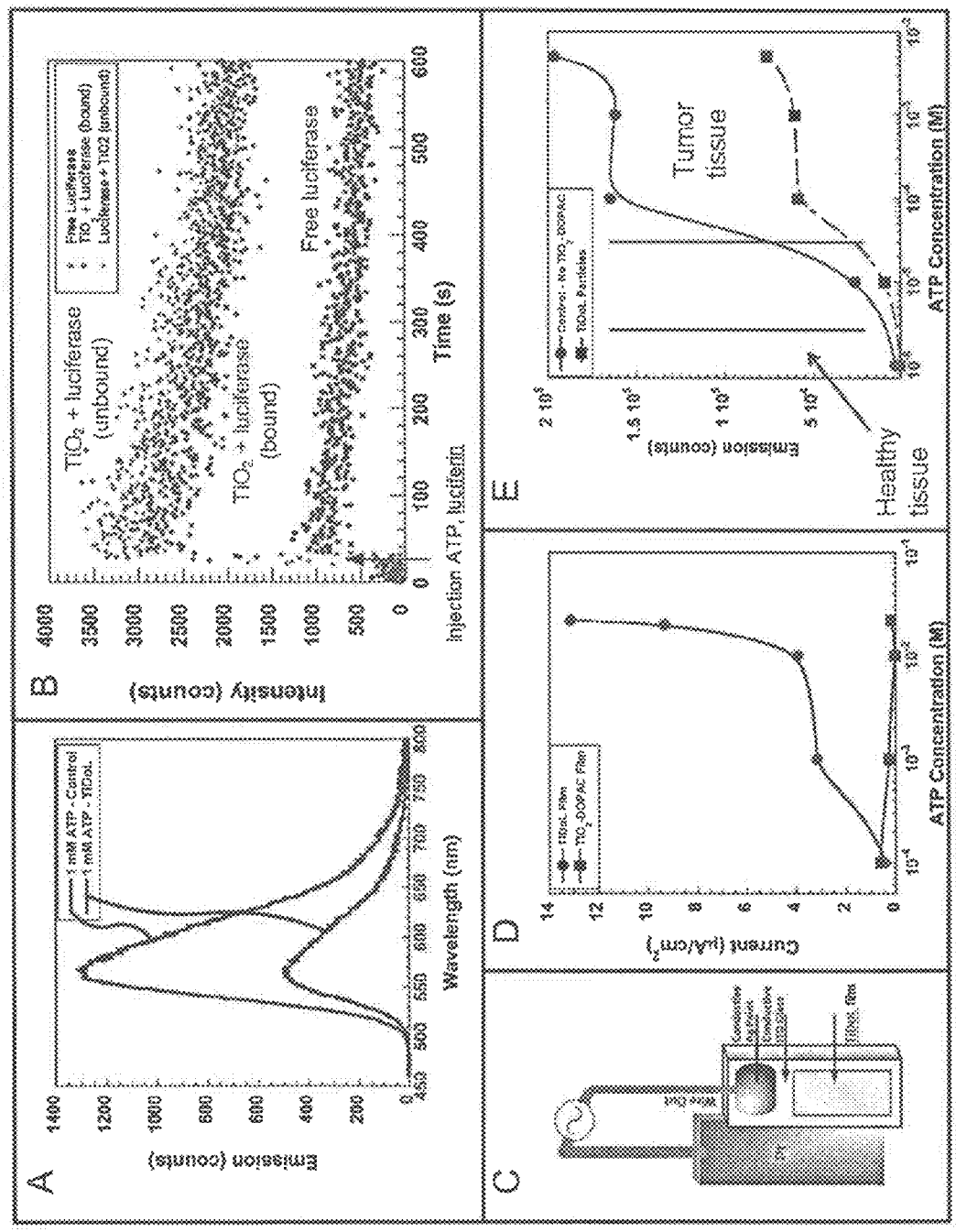
FIG. 7 panel A is a plot of emission of free luciferase activated by luciferin in solution is quenched by TiDoL nanoparticles.

FIG. 7 panel A is a plot of emission of free luciferase activated by luciferin in solution and quenched by TiDoL nanoparticles. FIG. 7 panel B is a plot of kinetics of light emission of free luciferase (10 nM) and luciferin (40 μM) in solution, free luciferase and luciferin in the presence of, but not conjugated to, an equimolar concentration of $TiO_2$-DOPAC (10 nM particles), and TiDoL nanoparticles (10 nM) and luciferin (40 μM) in solution.

FIG. 7 panel C is a schematic diagram of experimental luciferin induced current measurement setup in conjunction with FIG. 7 panel D which shows current generated by the luciferase mediated conversion of luciferin in TiDoL films as a function of ATP concentration. Current measurements were performed on the electrodes in a solution of 10 mM MES buffer (pH 6.1) and 5 mM hydroquinone purged with Ar. Independent of the quenching mechanism, both energy and electron transfer result in a charge separation and consequent formation of electrons in $TiO_2$ NPs. The appearance and the fate of electron-hole pairs generated with activation of TiDoL was measured by the current produced after injection of luciferin and variable amount of ATP to the electrolyte in an electrochemical cell composed of TiDoL film as a working electrode and a Pt counter electrode (FIG. 7 panel C and FIG. 7 panel D).

Appearance of a current upon luciferin and ATP injection is a consequence of charge separation that occurs either by luciferin light excitation of modified $TiO_2$ composites or by direct injection of the electrons from excited luciferin to $TiO_2$ NPs. Electrons formed in the conduction band of $TiO_2$ are further conducted through mesoporous thin film structure, support and external circuit to Pt electrode. Oxidized hydroquinone, used as a redox couple, will accept electrons at the Pt counter electrode and regenerate oxidized DOPAC or luciferin, maintaining the current flow. The current was measured over a range of ATP concentrations to verify that the differences in ATP concentration between healthy tissue (low micro-molar levels) and tumor tissue (low milli-molar levels) could be used as a means of targeting the generation of ROS to site of a tumor.

FIG. 7 panel E is a plot of bioluminescence emitted by the luciferase-mediated catalysis of luciferin at various concentrations of ATP. Minimal bioluminescence is emitted at ATP concentrations found in healthy tissue (low micro-molar levels) for both unconjugated luciferase and luciferase that has been conjugated to $TiO_2$-DOPAC NPs. Significant bioluminescence and bioluminescence quenching by TiDoL NPs is detected at ATP concentrations present in tumor tissue (low milli-molar levels). As seen in FIG. 7 panel E the current was increased with increasing ATP concentration in a dose-dependent manner echoing the dependence of TiDoL luminescence with ATP concentration.

FIG. 7 panels A-E convey the mechanism in which excitation of luciferin in close proximity of $TiO_2$ nanoparticles results in luminescence quenching in which the light is converted to the electron/hole pairs. Electron/hole pairs create potential, and subsequently the current enabling electrons accumulated on the platinum counter electrode to react readily with redox coupes such as hydroquinone or dissolved oxygen creating reactive $O_2^-$ species. FIG. 7 panel D shows that minimal bioluminescence and no current are observed when ATP is present in the concentrations comparable to those in the healthy tissue. Once ATP concentrations rises to the 100's of micro-molar/low milli-molar range that is characteristic of ATP levels found in tumor tissue, significant quenching of bioluminescence and consequent electric current with production of ROS was detected.

Figure 8:
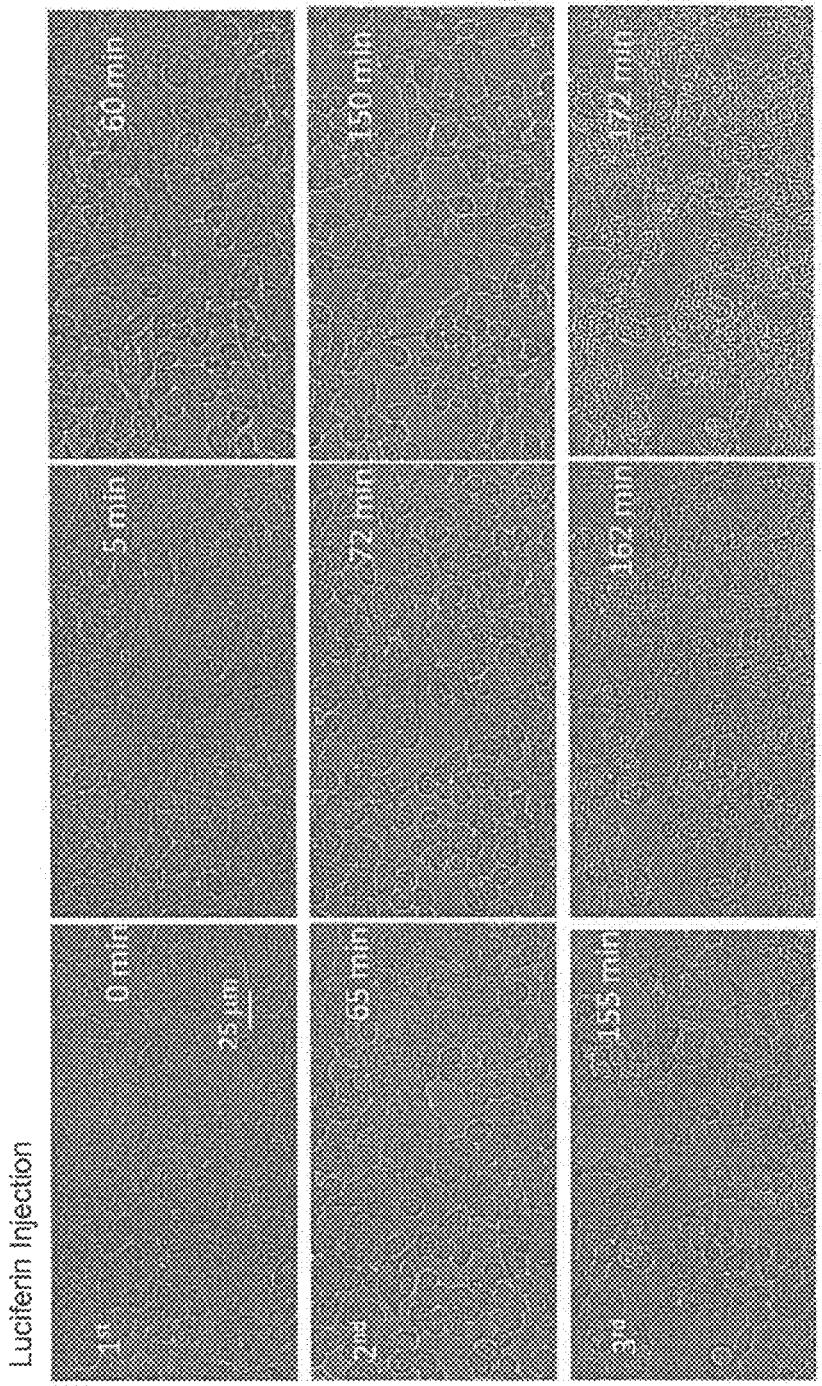
FIG. 8 shows optical microscopy images recorded at 20× magnification of time course of the morphological changes of HCT116 colon cancer cell line treated with 150 nM TiDoL in the presence of ATP (20 μM); cells are incubated in the McCoy culture media (absorption 600 nm); three aliquots of luciferin were added (15 μM final concentration) in 60 min interval to induce cell shrinking and budding.
Figure 9:
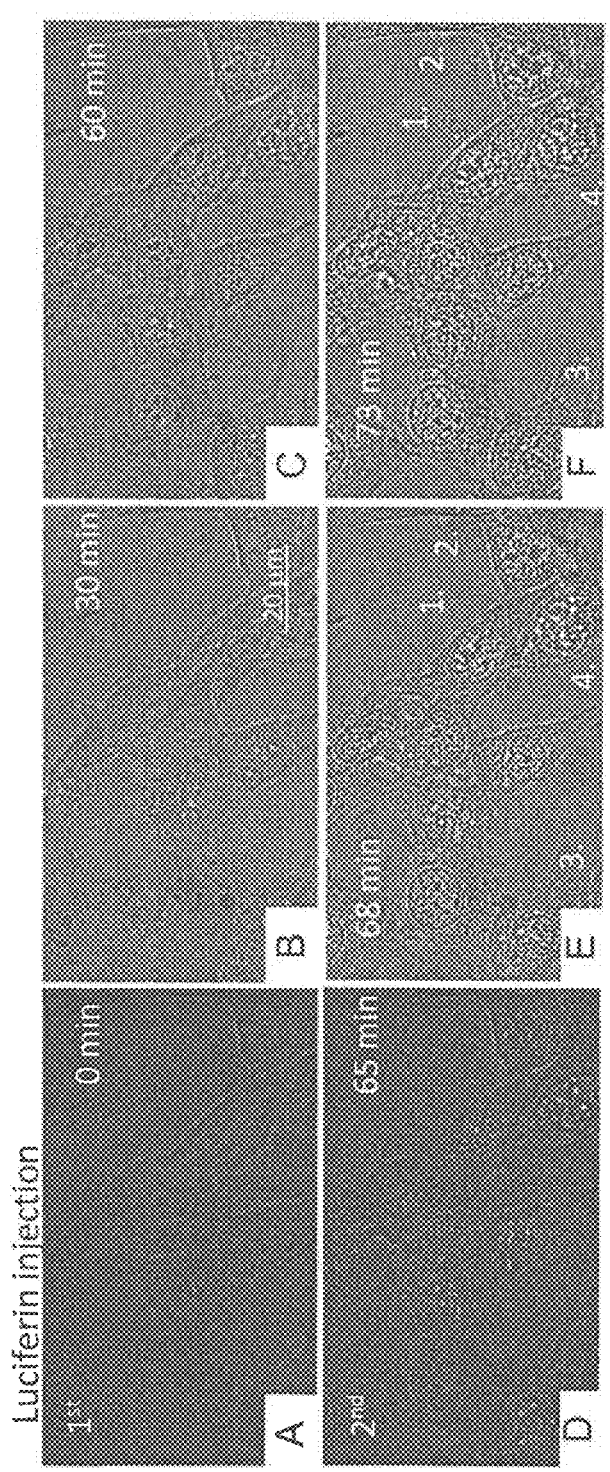
FIG. 9 panels A-F are optical microscopy images recorded at 40× magnification of time course of the morphological changes of HCT116 colon cancer cell line treated with 150 nM TiDoL in the presence of ATP (20 μM); cells were incubated in Hank Balanced Salt Solution (absorption 300 nm); two aliquots of luciferin were sufficient to cause cell budding.
Figure 10:
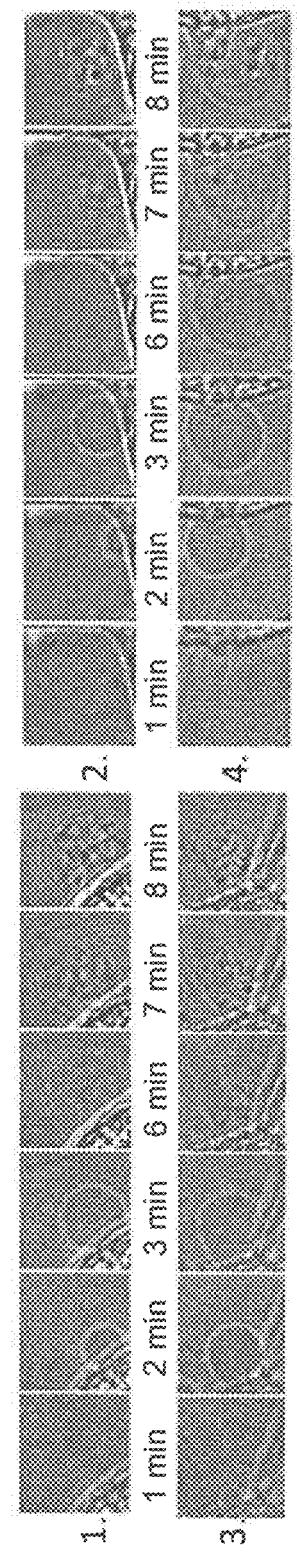
FIG. 10 are optical microscopy images at 126× magnification of time course of the morphological changes of HCT116 colon cancer cell line treated with 150 nM TiDoL in the presence of ATP (20 μM) showing time course of formation, growth and transfer of cell material to the apoptotic bodies after second luciferin injection.

The activity of self-powering TiDoL NPs within cell environment was tested in vitro and in situ. This approach brings to light key parameters that govern the mechanisms of transformation and requires only minimal operator intervention without interruption of the process or a risk of contamination. FIGS. 8-10 are optical images showing time course of the morphological changes of HCT116 colon cancer cell line treated with 150 nM TiDoL NPs in the presence of ATP (20 µM). After 20 min incubation, an aliquot of luciferin (15 µM final concentration) was injected and the response of the cells was monitored using transmission mode of confocal microscope.

FIG. 8 shows cells incubated in McCoy culture media (absorption 600 nm). Three aliquots of luciferin were added (15 µM final concentration) in 60 min interval to induce cell shrinking (cell interspace shaded in gray) and budding (shaded in pink). FIG. 9 panels A-F show cells incubated in Hank Balanced Salt Solution (HBSS) (absorption≤300 nm). The images of FIG. 8 were taken at 20× magnification, and FIG. 9 panels A-F were taken at 40× magnification. Two aliquots of luciferin were sufficient to cause cell budding. FIG. 10 includes optical images taken at 126× magnification showing time course of formation, growth and transfer of cell material to the apoptotic bodies after second luciferin injection.

FIG. 8 reveals the evolution of the cell transformations upon injection of luciferin to HCT116 colon cancer cells incubated with TiDoL NPs in cell culture media (light absorption λ≤600 nm) and in HBSS (no visible light absorption) at different times after injection of luciferin. Shortly (5 min) after first injection, cell rounding, shrinking and appearance of an enlarged intercellular spacing is observed. The cell shrinking continues reaching 85% of the initial surface coverage 50 min after luciferin injection, and after that time no additional changes were observed. Cell shrinking accompanied by their slow detachment from the well support (manifested as a change of the focus plane) is indicative of cell dying. Cells, however, remain with an intact plasma membrane, indicative of the typical morphology of apoptosis.

Injection of the second aliquot of luciferin again accelerates changes in cell morphology. Cells shrink to a 60% of their initial surface coverage 85 min after injection of the second dose of luciferin, and blabbing of the cells is observed throughout the well. Despite massive shrinking, cells remain contained within an intact membrane and are interconnected with stretched actin across large empty intercellular spacing. It is important to note that additional addition of ATP did not enhance further changes in the cell morphology. Injection of the third aliquot of luciferin very quickly causes even more drastic changes, and 7 min after injection, cells start budding with a formation of apoptotic bodies. Formation of these membrane-enclosed apoptotic bodies is a critical aspect of luciferin induced cell death as apoptotic bodes are phagocyted and digested by nearby resident cells. Concomitantly, nuclear membrane starts darkening and nuclear chromatin starts condensing.

This sequence of events was even faster and more clearly observed when cells are exposed to TiDoL/ATP/luciferin in Hanks' balanced salt solution (HBSS) that does not attenuate 560 nm light. FIG. 9 panels A-F show magnified views of the events that are occurring after luciferin injection. Injection of luciferin is accompanied by darkening of the field of view due to the absorption of luciferin in the visible part of the spectrum (λ<520 nm). After the brightness is restored 30 seconds after the injection, saddle shrinking of the cells is observed along with increasing of the contrast of the nuclear membrane and the chromatin within the nucleus. Subsequent injection of an aliquot of luciferin leads to quick appearance (3 min) of apoptotic bodies, enhancing the contrasting of the cell features and reorganization of the cell chromatin. Soon after (6 min after $2^{nd}$ luciferin injection) packaging of cellular contents into membrane-enclosed apoptotic bodies is observed (FIG. 10). These apoptotic bodies, which encapsulate the cell material, are being recognized, engulfed and ingested by microphages in vivo that are involved in the clearance of apoptotic cells during the stage of apoptotic body-recognition and during the formation of early phagosomes. It is important to note that apoptotic processes were not limited to the imaging area. Post-treatment imaging of the cells in the distant areas that were not exposed to imaging light showed the same signs of apoptosis with a near 100% efficiency as those in the imaged areas), indicating that the radicals formed upon interaction of luciferin and TiDoL NPs are responsible for inducing cell apoptosis.

Figure 11:
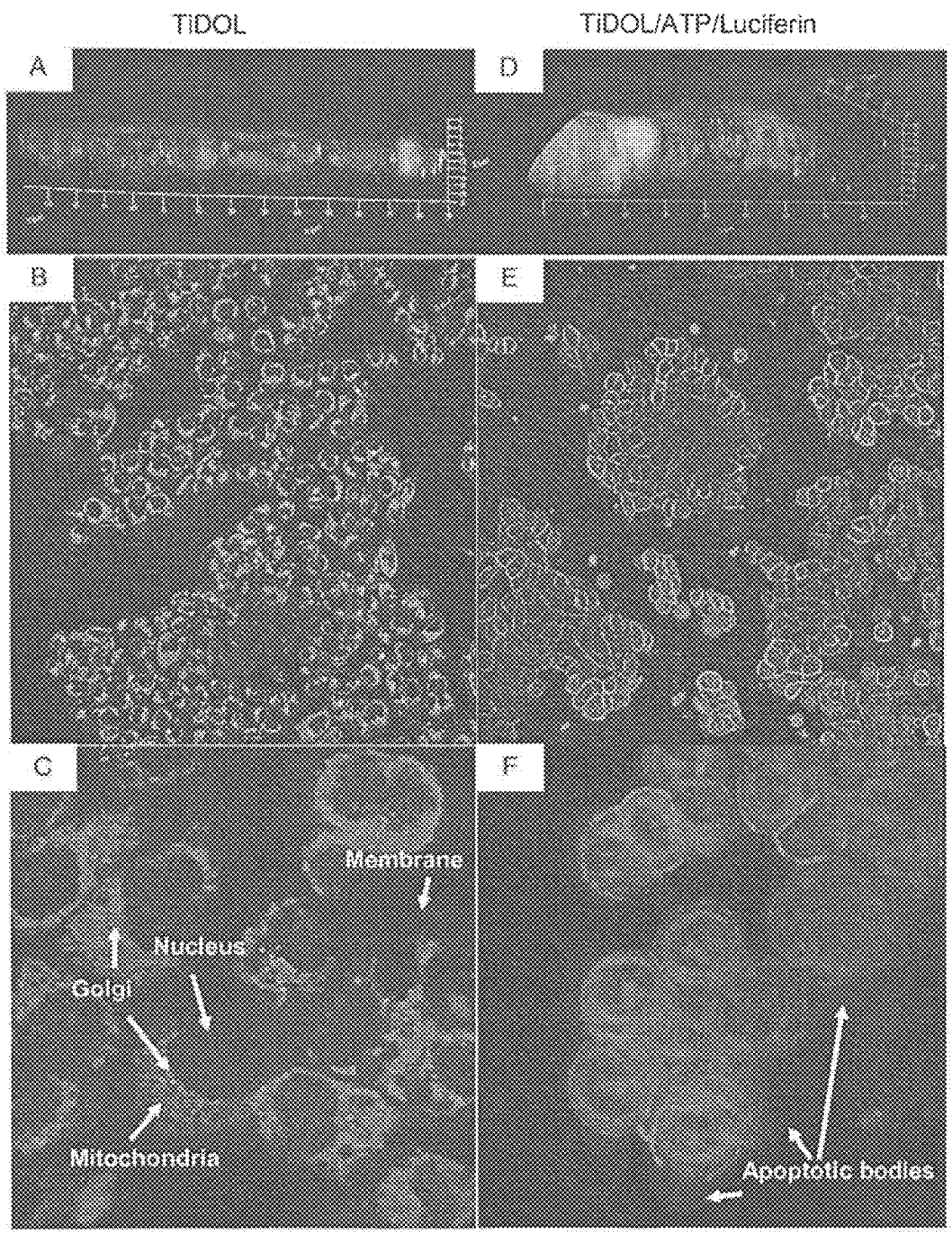
FIG. 11 panels A-F are optical images of morphological changes in HCT116 cells upon treatment with TiDoL/ATP/luciferase observed staining of the membrane and trans-Golgi with WGA labled with green ALEXAFLUOR® 488 and mitochondria staining using MITOTRACKER® red twelve hours after treatment. Panels A-C are healthy cells imaged in HBSS after treatment with 150 nM TiDoL, and panels D-F are cells treated with 150 nM TiDoL in the presence of 20 μM ATP and two aliquots of 15 μM luciferin added in the intervals of 30 min. Panels A and D are 3-dimensional images of the cells. Panels B and E are optical images taken at 20× magnification, while panels C and F are optical images taken at 100× magnification.

In order to further understand the process of cell death of HCT116 cells in vitro induced by TiDoL/ATP/Luciferin, the activity of the TiDoL NPs was studied ex situ using cells staining. FIG. 11 shows morphological changes in HCT116 cells upon treatment with TiDoL/ATP/luciferase observed staining of the membrane and trans-Golgi with wheat germ agglutinin (WGA) labled with ALEXAFLUOR® 488 and mitochondria staining using MITOTRACKER® red dye twelve hours after treatment. Panels A-C depict healthy cells imaged in HBSS after treatment with 150 nM TiDoL, and panels E-F depict cells treated with 150 nM TiDoL in the presence of 20 µM ATP and two aliquots of 15 µM luciferin added in the intervals of 30 min. Panels A and B are 3D images of the cells. Panels B and E were taken with 20× magnification, while the panels C and F were taken with 100× magnification.

Expanding further, the HCT116 cells were incubated with TiDoL NPs or controls and activated by two sequential aliquots of luciferin for 30 min in $CO_2$ incubator. Subsequently, live cells were washed and stained using fluorescent WGA, labled with green ALEXAFLUOR® 488 and MITOTRACKER® red dye. Cell membranes of human colorectal cancer cells, including HCT116 cell line, express multiple glycoprotein ligands allowing the use of WGA for sensitive imaging of cytoplasmic membranes in HCT116 cell line. In addition, fluorescent WGA was also used stain the Golgi apparatus as cisternae, as the trans face of Golgi membrane stacks participate in glycosylation of proteins that also bind WGA.

MITOTRACKER® red, a cationic red-fluorescent dye binds negatively charged mitochondria in live cells, and was used for labeling of mitochondria. It possesses a reactive chloromethyl group that forms a covalent bond with free thiols in proteins and peptides, retaining labeling thiol containing proteins even after mitochondrial depolarization. FIG. 11 shows stained HCT116 cells incubated with TiDoL NPs before (panels A-C) and after treatment with luciferin (panels D-F). All the cells incubated with TiDoL only (panels A-C) remain viable and have well defined cytoplasmic membranes, Golgi apparatus, and polarized mitochondria. 3D images (panels A and D) also show that cells are spread and adhered to the support having sizes ranging from 30-40 µm and the thickness ranging 2-4 µm (panel A).

After the treatment with luciferin cells shrink laterally and thicken, detach from the support, however, they still show strong and intact cytoplasmic membranes. The Golgi apparatus disappears, the inner nuclear membrane becomes permeable and nuclear region becomes barely identifiable. All the content of mitochondria and thiol containing proteins becomes uniformly distributed throughout the cytoplasmic and nuclear regions. There is, however, an indication of the existence of an inner nuclear membrane that is faintly visible using WGA imaging. Importantly, new enclosed pressurized membrane features outside the cells suggestive of apoptotic bodies are also observed. Some of the cells start also pouring their content, including MITOTRACKER® labeled thiol-containing peptides and proteins, into apoptotic bodies.

Figure 12:
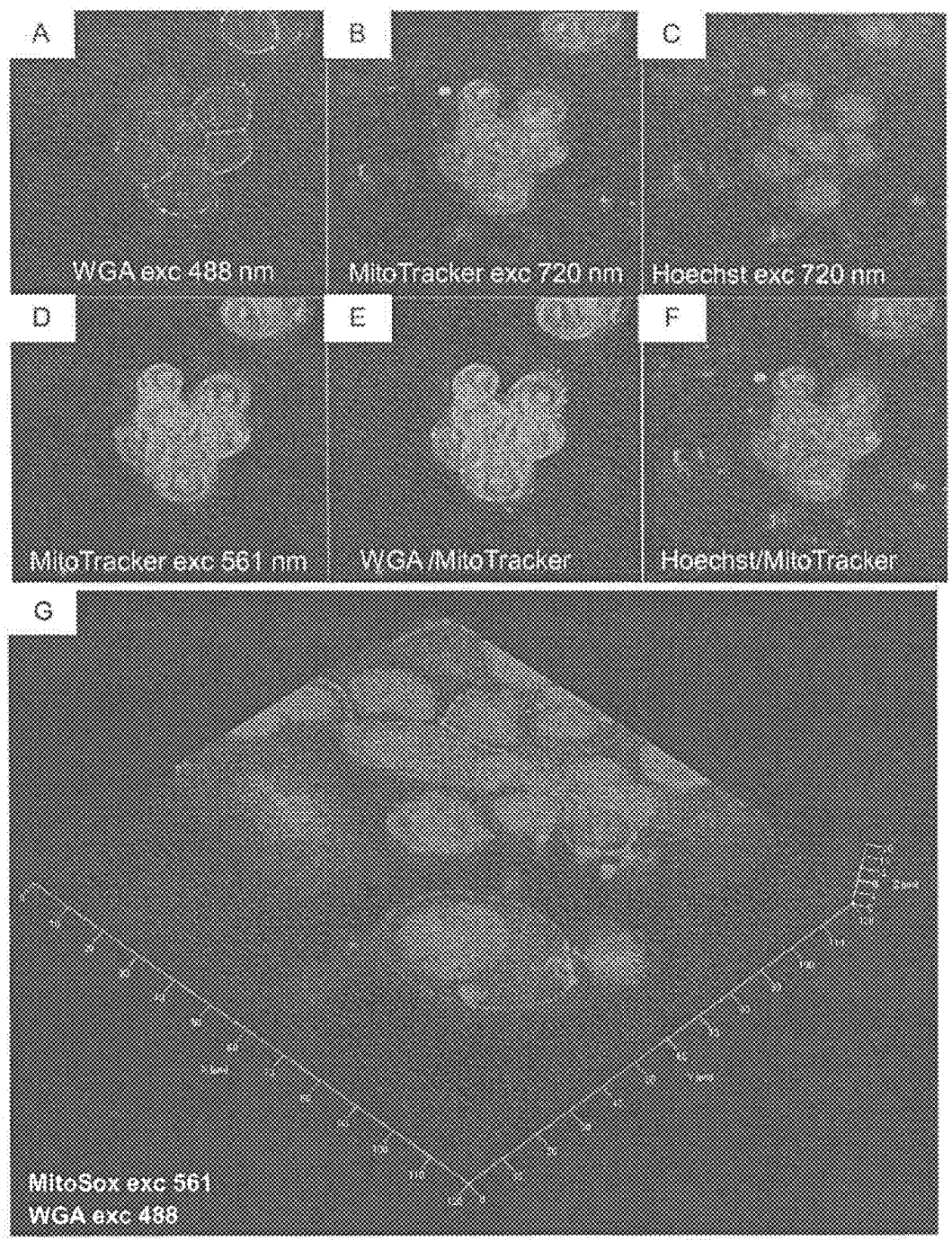
FIG. 12 panels A-F are optical images of HCT116 cells after treatment with TiDoL/ATP/luciferase observed using staining of the membrane with WGA dye (panel A), thiol containing peptides with MITOTRACKER® dye excited using two photon excitation at 720 nm (panel B), double stranded (ds) DNA with HOECHST® 33342 dye (panel C), with MITOTRACKER® excited at 561 nm (panel D), with wheat germ agglutinin (WGA, labeled with green Alexa Fluor® 488) and MITOTRACKER® (panel E), and with HOECHST® and MITOTRACKER® (panel F) twelve hours after treatment.

Further study of apoptotic pathway was investigated by imaging the nuclei using HOECHST® 33342 stain, a dye often used to distinguish condensed pycnotic nuclei in apoptotic cells. FIG. 12 panels A-F are optical images of HCT116 cells after the treatment with TiDoL/ATP/luciferase observed using staining of the membrane with WGA, thiol containing peptides with MITOTRACKER®, and ds DNA with HOECHST® 33342 twelve hours after treatment. FIG. 12 panel G is a 3D image of treated cells stained with MITOSOX® for obtaining distribution of superoxide radicals within treated cells.

The images of the group of the cells of FIG. 12 were obtained by laser excitation using 488 and 561 nm as well as two photon excitation using 720 nm light. The image obtained using WGA and MITOTRACKER® depict intact membrane and depolarized mitochondria with protein contents throughout both cytoplasmic and nuclear region, while two photon imaging using HOECHST® shows pycnotic nuclei, typical of apoptotic cell death. Nuclear chromatin condensation and chromosomal DNA fragmentation are well-described by key features in apoptosis. The chromatin condensation is microscopically visible after staining with the blue-fluorescent HOECHST® 33342 dye staining as dense chromatin aggregates typically near to the nuclear membrane is observed. Condensed chromatin is the result of a specific DNA fragmentation in the nuclei via cleavage by endogenous endonucleases and appears as pycnotic nuclei. The large nuclei and scant cytoplasm observed in two photon measurements are also indicative of apoptosis.

Presence of DNA can be also observed in apoptotic bodies co-localized with thiol containing proteins outside the cell compartment. MITOSOX® red staining, that is widely used as a marker to evaluate apoptosis in various cell types, also indicates enhanced oxidative stress (superoxide was below the detection limit in the healthy cells). High fluorescence of oxidized MITOSOX® dye was detected in the nuclear region of TiDoL/luciferin treated cells and in apoptotic bodies which can be attributed to the higher intensity of the MITOSOX® red fluorescence when bound to ds DNA rather than to the higher concentrations of superoxide radical in these cell regions. MITOSOX® fluorescence was undetectable in viable cells.

Morphological changes observed in FIG. 12 (cell shrinking, detachment from the support, cell budding, membrane-enclosed apoptotic bodies, intact cell membrane, pycnotic nuclei and high rate of formation of superoxide radicals) all conform with apoptotic pathway of cell death upon bioluminescence initiated in vitro treatment of the cancer cells using TiDoL NPs. These results clearly indicate that the TiDoL NPs trigger apoptosis in cancer cells in the presence of luciferin, as programmed cell death is characterized by degradation of cell components within apoptotic cells while their plasma membrane remains intact. Since it is believed that apoptosis is physiologically advantageous way of cell death because apoptotic cells can be removed by phagocytosis and digested by nearby resident cells before they lose their outer permeability barrier, thus preventing induction of inflammatory responses to the dying cells and potential harmful secondary effects, the TiDoL NPs can be used to treat cancer with minimal or no side-effects.

In order to enhance the retention of TiDoL NPs in the tumor region and mediate site selective light activity a composite of TiDoL NPs with monoclonal antibody C225 (TiDoL-C225) was synthesized. C-225 is a chimeric monoclonal antibody directed against the epidermal growth factor (EGFR). C225 (or CETUXIMAB®) binds to the extracellular domain of the EGFR, thereby preventing the dimerization of the receptor resulting in an inhibition in signal transduction, anti-proliferative effects and hindering of EGFR-dependent primary tumor growth and metastasis. EGFR is overexpressed on the cell membranes of various solid tumors and is highly expressed on the surface of HCT116 cell line. Antibodies provide a highly selective specificity to the nanoparticles, increasing their retention on targeted cells that express cognate antigens on the membrane surface. Hence, composites are activated only in the close proximity to biological targets of interest, such as cancerous cells, and are not retained in nearby healthy cells.

In particular embodiments, TiDoL NPs were modified with C225 by adding 10 µl of 10 mg/mL DOPAC (Sigma-Aldrich, St. Louis, Mo.) to 125 µl of 13.3 µM C225 (2 mg/ml C-225/Erbitux, Eli Lilly, New York, N.Y.) anti-EGFR monoclonal antibody in nitrogen box. 20 µl of already mixed 0.5 mL of 10 mg/mL EDC was added, and 0.5 mL of 10 mg/mL NHS under nitrogen atmosphere. Solution was incubated for two hours at room temperature under nitrogen. Then, the solution was washed four times with PBS in a centrifuge. After the final wash, the final volume was adjusted to 125 µl and 300 µl of 6.2 µM TiDoL was added. This preparation makes a final TiDoL-C225 NP solution with a concentration of 4.15 µM with a 0.28 µM concentration of free C225, which is approximately 5% excess.

Figure 13:
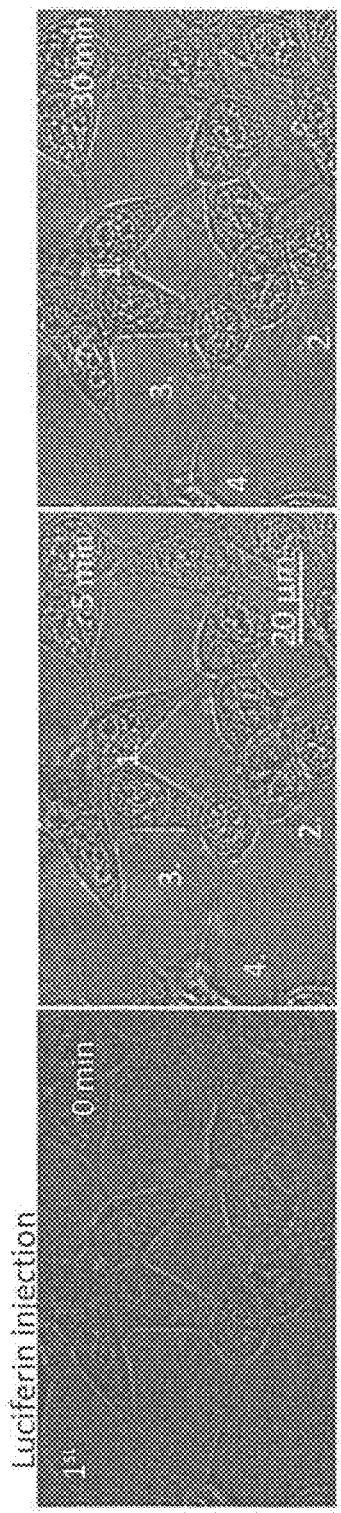
FIG. 13 are optical images recorded at 40× magnification of time course of the morphological changes of HCT116 colon cancer cell line treated with 150 nM TiDoL-C225; all conditions are the same as in FIG. 5 and budding of the cells starts 30 seconds after first luciferin injections.
Figure 14:
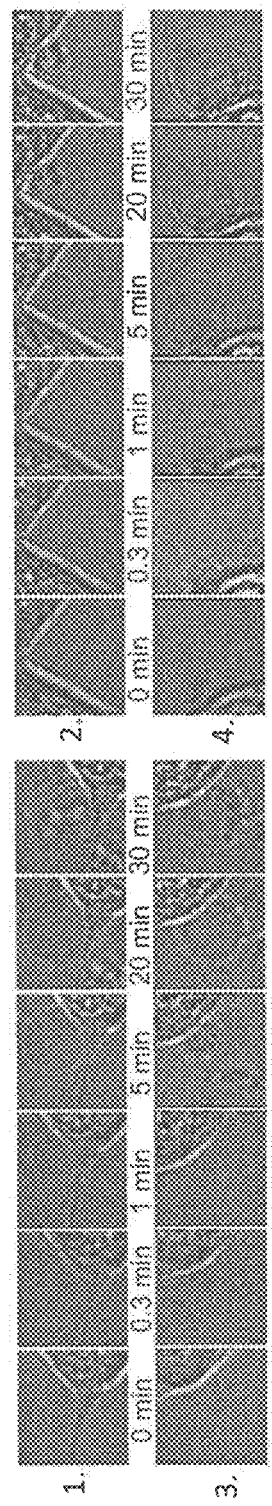
FIG. 14 are optical images at 126× magnification of time course of formation, growth and transfer of cell material to the apoptotic bodies after first luciferin injection.

FIG. 13 are optical images of time course of the morphological changes of HCT116 colon cancer cell line treated with 150 nM TiDoL-C225 NPs. All conditions are the same as in FIG. 9 and budding of the cells starts 20 seconds after first luciferin injections. FIG. 14 are optical images at 126× magnification of time course of formation, growth and transfer of cell material to the apoptotic bodies after first luciferin injection.

Integration of C225 with TiDoL NPs resulted in a nanoconjugate that induced cell budding as soon as 20 seconds after luciferin injection and 5 minutes after injection affected all observed cells (FIG. 13). Soon after cell budding changes were observed similar to those observed in TiDoL NPs treated cells, darkening of the nuclear membrane and enhancement of the image contrast as a result of chromatin rearrangement. Due to this rapid budding the cells do not have the time, however, to go through the shrinking phase, however they still show strong and intact cytoplasmic membranes that extends to apoptotic bodies. Cells start filling of their content into the apoptotic bodies 20 minutes after budding, which is much slower compared to the treatment with TiDoL NP conjugates in the absence of C225 when budding occurred at much slower timeframe. This is probably due to the timeframe required to fulfill signaling cascade involved in transferring of cell material to the apoptotic bodies.

Figure 15:
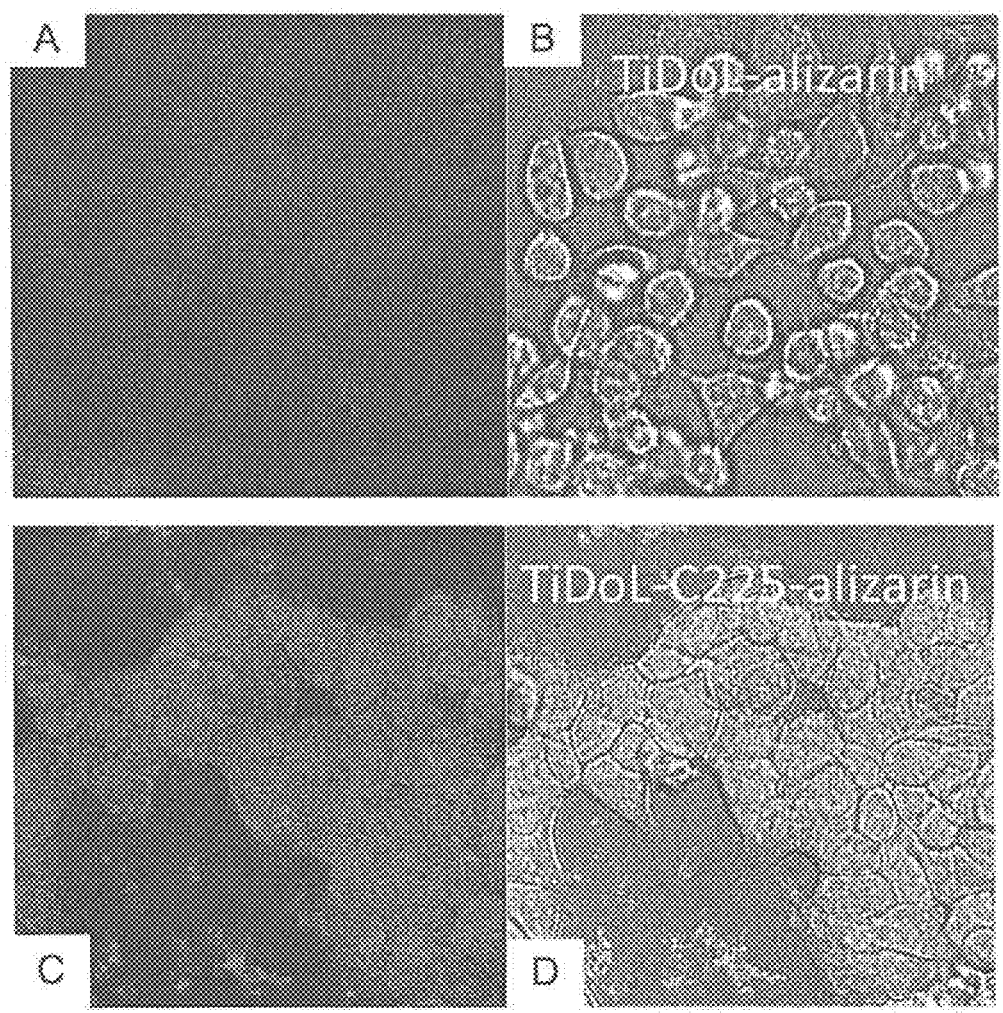
FIG. 15 panel A is a laser excitation (560 nm) image and panel B is an optical image of TiDoL NPs which are bound with alizarine dye which can enable visualization of the TiDoL NPs absorbed on HCT116 cells, and FIG. 15 panels C-D are laser excitation and optical images, respectively of TiDoL NPs coupled to C225 antibody and alizarine dye absorbed on HCT116 cells.

In order to visualize antibody facilitated adsorption (targeting) of TiDoL-C225 NPs to the cells the TiDoL-C225 NPs were modified with alizarine, an enediol dye that changes absorption and fluoresce of $TiO_2$ nanoparticles. FIG. 15 panels A and B are optical and laser excitation images, respectively, (laser excitation 561 nm and imaging at $\lambda$>570 nm) of membrane bound TiDoL NPs on HCT116 cells, while FIG. 15 panels C and D are optical and laser excitation images, respectively, of membrane bound of TiDoL-C225 NPs on HCT116 cells. The NPs are visualized by imaging of alizarine bound to the $TiO_2$ nanoparticles under the same conditions.

While faint image of untargeted TiDoL NPs suggest nonspecific binding of the complex to the cell membrane, C225 labeled TiDoL shows strong red luminescence confined to the HCT116 cell membrane, indicating strong adsorption of TiDoL-C225 NPS to the cell surface with expressed EGFR receptors. Injection of luciferin first quenches the red luminescence of alizarin $TiO_2$ complex while enhancing the intensity of luminescence in the green part of the spectral region, which is in the agreement with the hypsochromic shift of the charge transfer luminescence due to filling of the lowest excited electron/hole states.

Figure 16:
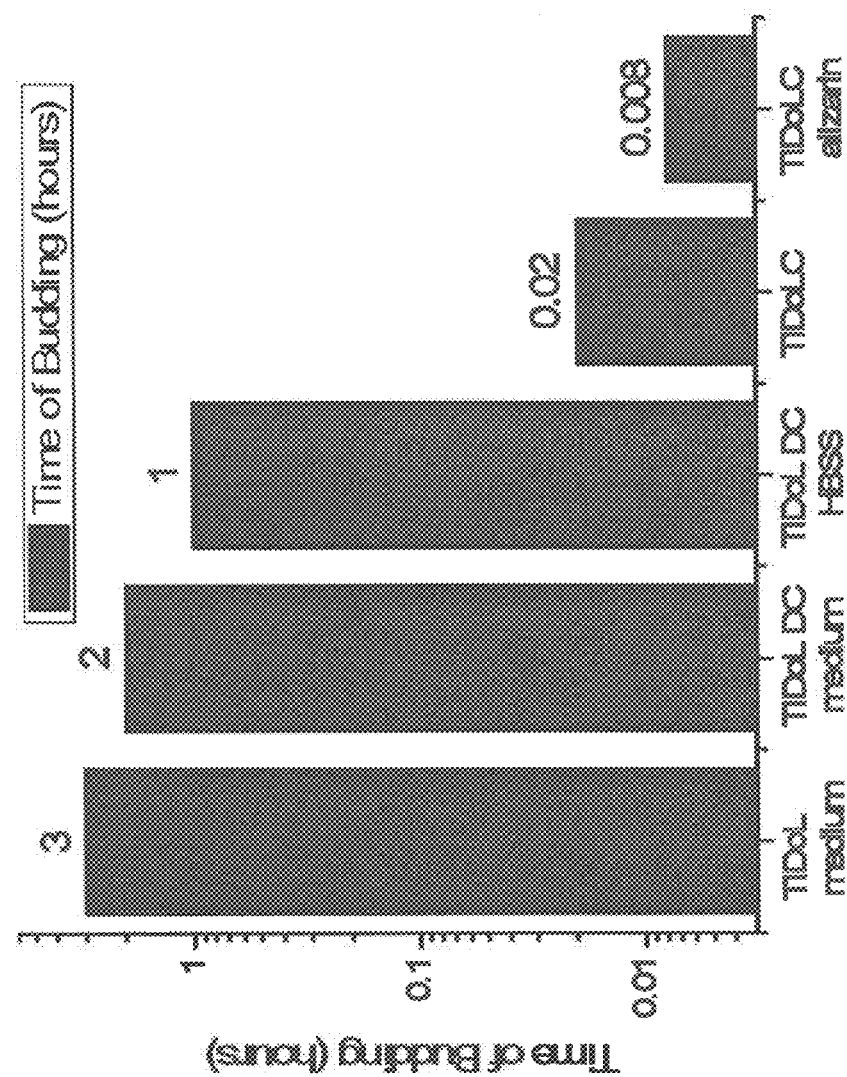
FIG. 16 is a bar chart of time of budding of HCT116 cells treated by different NPs and activated by luciferin (time of budding is an indicator of cell death).

Only 30 seconds after luciferin injection, on average, the cells start budding and die without pouring their content into apoptotic bodies. The accelerated dying of the cells is attributed to the high concentration of light induced radical species due to exact overlap of $TiO_2$-alizarine absorption and luciferase mediated luciferin fluorescence at 560 nm. On the other hand alizarin-TiDoL-C225 does not show binding to EGFR-non transformed fibroblast cells. The composite does not produce cell budding in fibroblast cells even after 3 doses of luciferin in the presence of ATP in the concentrations available in the healthy cell tissues. TiDoL-C225 NPs also induced cell death at the concentration as low as 10 nM (1.1 µg/ml $TiO_2$) compared to 20 nM TiDoL NPs that was sufficient to induce cell death under the same conditions. FIG. 16 is a bar chart of time of budding of HCT116 cells treated by different NPs and activated by luciferin. Time of budding is an indicator of cell death.

To demonstrate the applicability of the NPs described herein in vivo, a single dose of 50 µl TiDoL (6 µM), TiDoL-C225 (4 µM) was administered with appropriate controls into nude mice bearing the aggressive HCT116 tumor model. Luciferin was administrated intraperitoneally, one dose an hour and other 48 hours after TiDoL treatment. Significant differences in cancer growth between the tumors with and without luciferin administration in TiDoL treated nude mice were observed, as shown in FIG. 17.

Figure 17A:
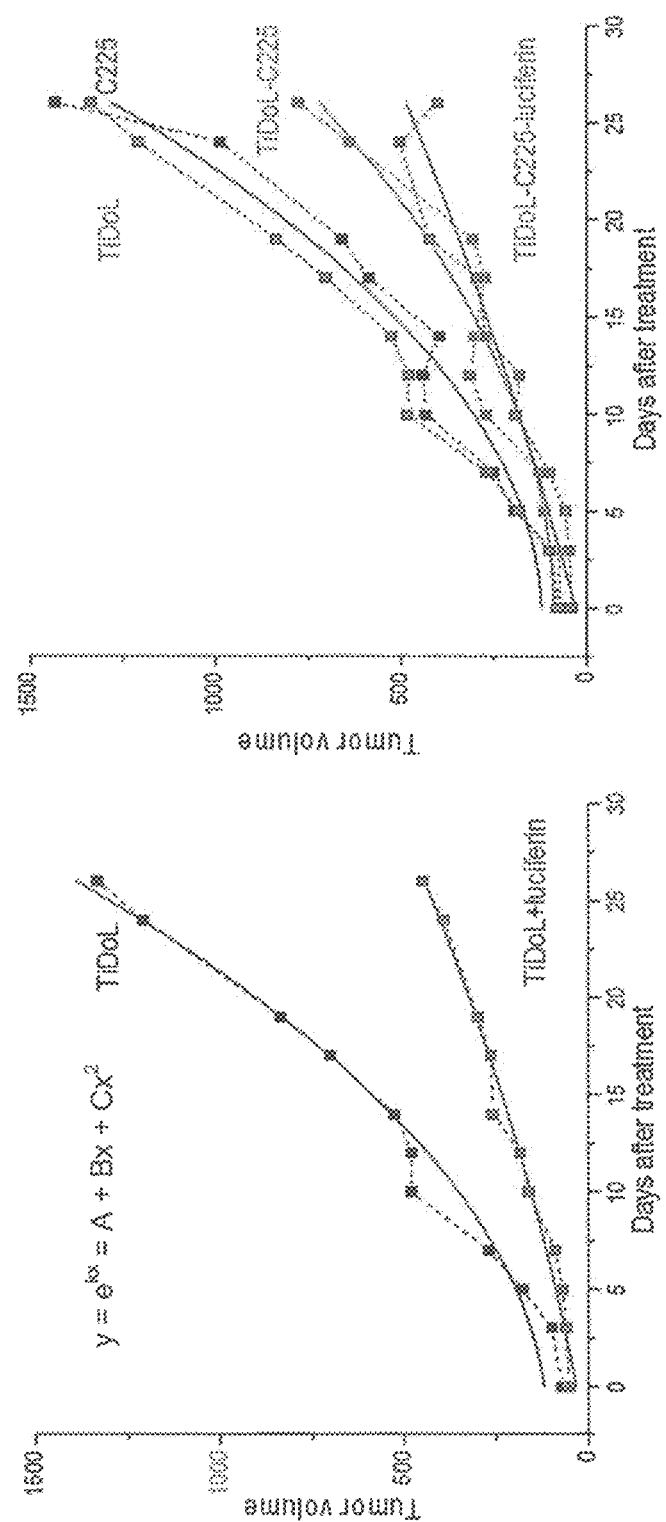
FIG. 17A are plots showing evolution of tumors treated by TiDoL (left plot) and TiDoL-C225 (right plot) with and without activation with luciferin, each point is an average of six measurements and the data are fitted with quadratic polynomial dependence as an approximation of exponential growth.

FIG. 17A shows plots of evolution of tumors treated by TiDoL (left plot) and TiDoL-C225 (right plot) without activation with luciferin. Each point is an average of six measurements. Data are fitted with quadratic polynomial dependence as an approximation of exponential growth. While those cells that did not receive luciferin continue exponential growth, the progress of luciferin treated tumors slows down and 26 days after the treatment becomes three times smaller on average compared to those that did not receive luciferin. Cell growth of all tumors was fitted with a polynomial (parabolic) function and was found that cell growth in control tumors is dominated by fast quadratic term (C>B), while those administered with luciferin show altered trend with slow linear growth becoming dominant (C<B). These findings suggest existence of the process that competes with the cell growth upon activation of TiDoL NPs in the tumors with luciferin, limiting proliferation rate of the tumor.

Figure 17B:
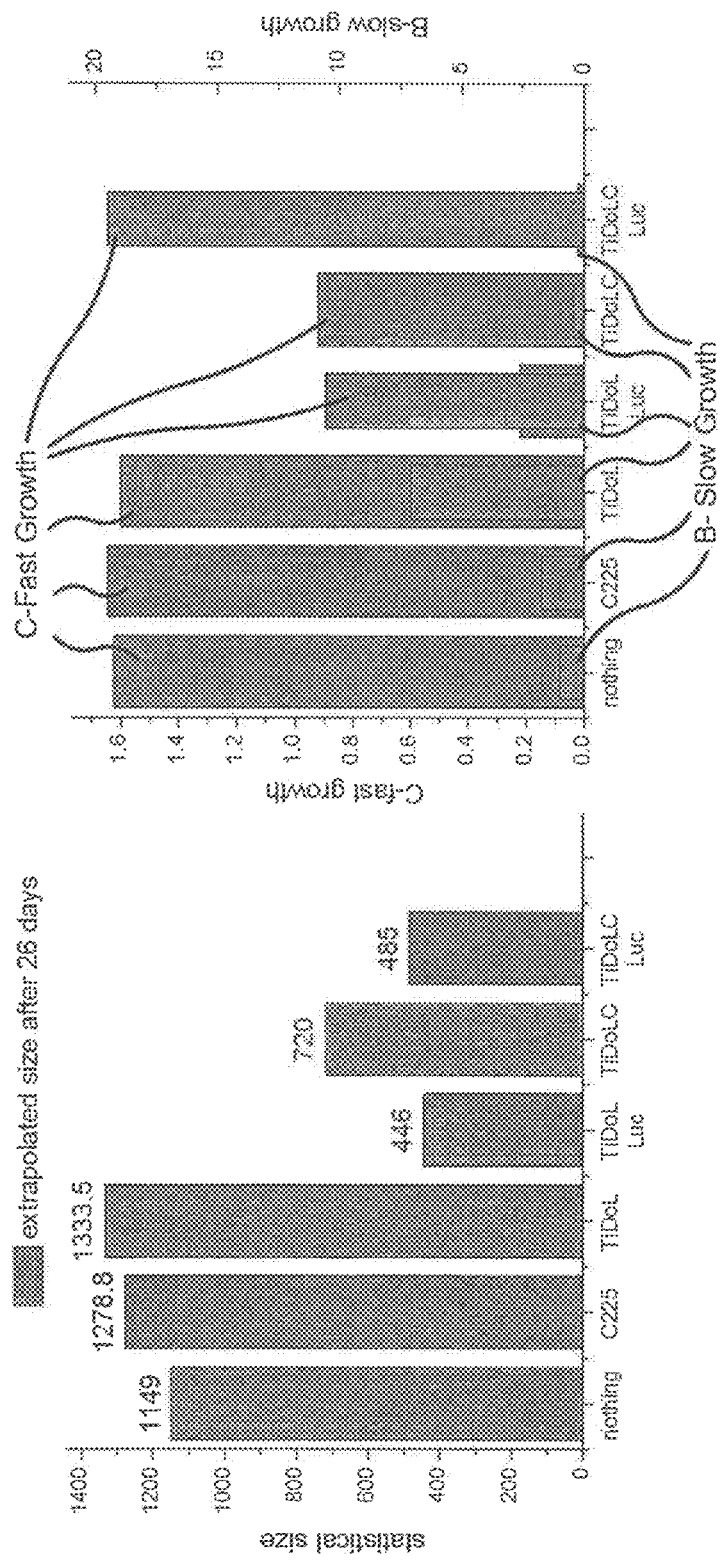
FIG. 17B are histograms of tumor sizes 26 days after the treatment of nude mice (left plot) in conjunction with histogram of the linear and quadratic coefficient of tumor growth (right plot) obtained from data fitting.
Figure 17C:
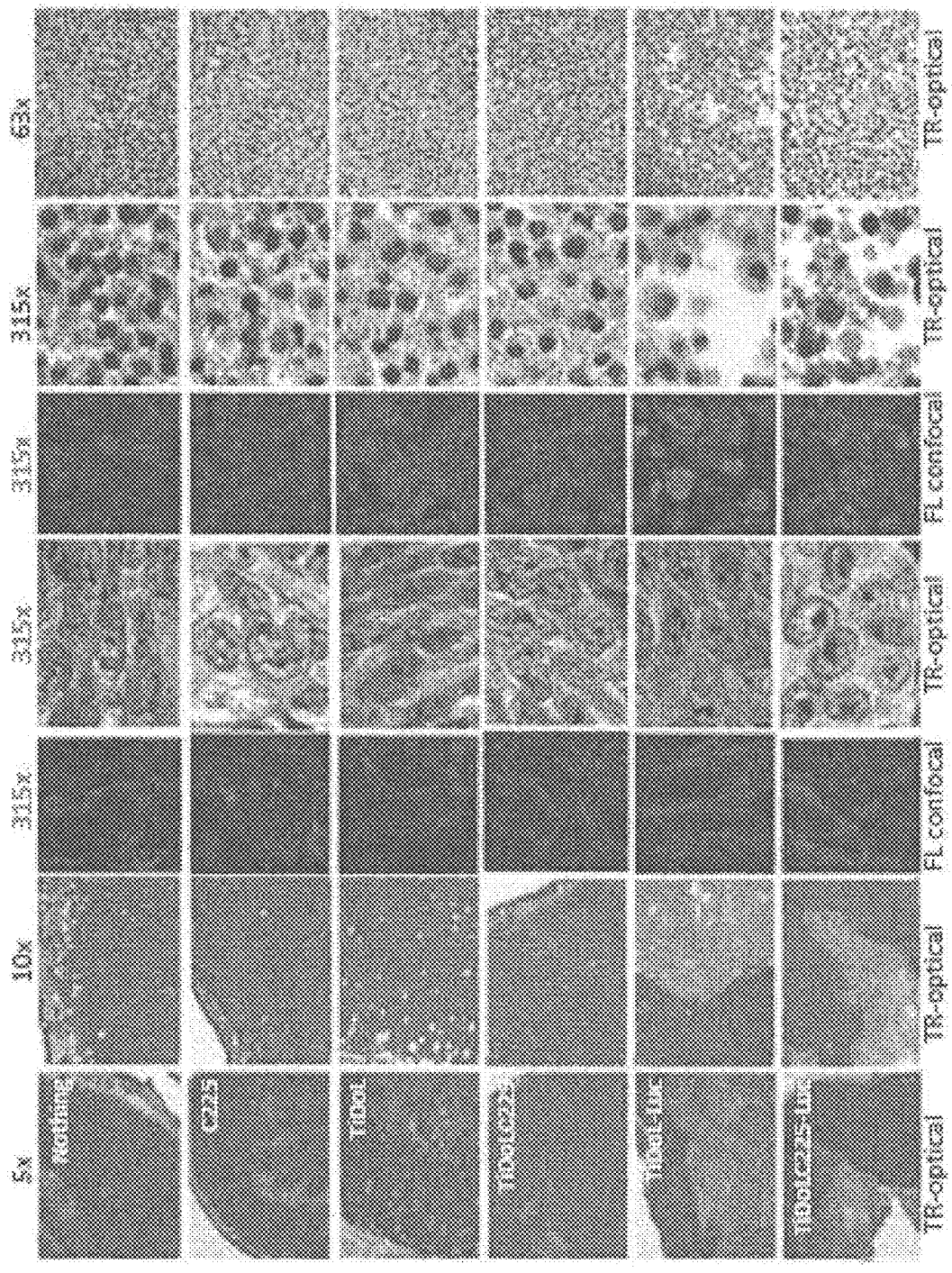
FIG. 17C are transmission optical (TR-optical) and laser confocal fluorescence (FL-confocal) images of H&E stained tumor slices obtained by sectioning of the tumors 26 days after the treatment at different magnifications.

FIG. 17B shows histograms of tumor sizes 26 days after the treatment of nude mice in conjunction with histogram of the linear and quadratic coefficient of tumor growth obtained from data fitting. FIG. 17C shows a transmission optical (TR-optical) and laser confocal fluorescence (FL-confocal) images of H&E stained tumor slices obtained by sectioning of the tumors 26 days after the treatment at different magnifications.

Administration of targeted TiDoL NPs modified with C225 antibody also resulted in limiting growth of the tumor when treated with luciferase. Twenty six days after treatment the tumors show three times smaller size on average compared to those treated with antibody C225 only. The treatment of the tumor with TiDoL-C225 NPs only, without administering luciferin, also slows down the growth rate of the tumor on average, however, to a lesser extent than both TiDoL luciferin NP or TiDoL-C225 luciferin NP treated tumors (FIG. 17C). Although the overall size is about 1.5 times smaller than the size of the controls, again fitting of the growth rate using Taylor series of the exponential function shows that these cells still have dominant fast quadratic growth (C>B) just like in C225 control and non-treated tumors. Intraperitoneal addition of luciferin again reverses the growth rate mechanism (B>C) fostering linear growth of tumors and luciferin treated tumors grow to 30% of the size realized in the controls (C225, not treated or TiDoL).

Histologic analysis of control not activated tumors 26 days after the treatment shows that tumors have large area of growing cancerous cells and smaller cell necrosis confined to the center of the tumor (FIG. 17C, 5× and 10× magnification). On the other hand, cells treated by TiDoL NPs and TiDoL-C225 NPs and activated with luciferin show large dead and denuded areas, respectively. Large denuded areas in TiDoL-C225 NPs treated luciferin activated tumors suggest macrophage assisted clearance of dead cells. These areas are surrounded by thin belt of viable cancerous cells. Growing cells in all specimens show faint hematoxylin stained DNA/RNA distributed throughout the nuclei and condensed in a highly stained nucleolus. Necrotic areas, however, show small condensed and pycnotic nuclei in condensed cells. The size of necrotic cells in luciferin activated treated cells is even smaller compared to the size of unactivated cells and show scant cytoplasm compared to untreated and nanoconjugate treated cells without activation. These cells also show large denuded areas as a consequence of phagocytosis that are in the case of TiDoL treated cells very clean and in the tumors treated with TiDoL-C225 NPs show more residual debris adjacent to completely removed parts of the tumor. Some of the debris contains DNA/RNA, while others contain mainly proteins stained by eosin.

While the above examples were focused on targeting and treating colon cancer cells using C225 antibody, the C225 antibody can be replaced with any other antibody to target any type of cancer, as described herein. For example, A172 glioblastoma brain tumor cells are known to express interleukin-13 (IL-13) receptor on a cell membrane of the glioblastoma cells. The C-225 body can be replaced with anti-IL13 antibody on the biocatalyst coupled MOX NPS to target and treat the glioblastoma cells.

Figure 18:
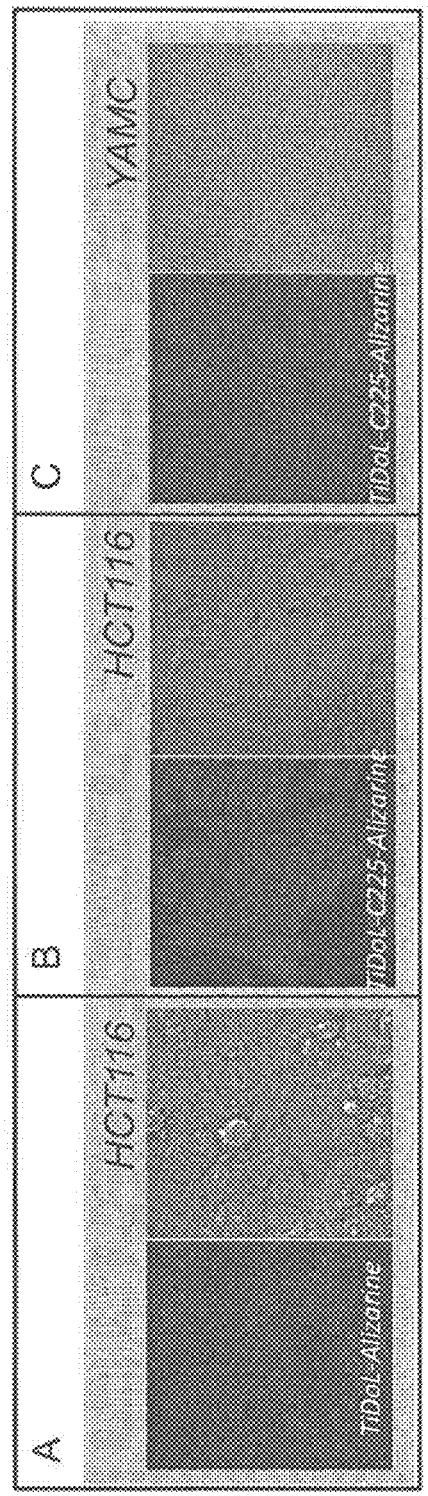
FIG. 18 panels A and B shows an optical fluorescence image (left) and a transmission electron microscopy (TEM) image (right) of colorectal carcinoma (HCT116) cells treated with TiDoL bound to alizarine dye without C225 antibody (panel A) and with C225 antibody (panel B).

FIG. 18 panels A and B shows an optical fluorescence image (left) and a transmission electron microscopy (TEM) image (right) of colorectal carcinoma (HCT116) cells treated with TiDoL bound to Alizarine dye without C225 antibody (panel A) and with C225 antibody (panel B). Panel C includes an optical fluorescence image (left) and a TEM image (right) of young adult mouse colonocyte or colonic epithelial (YAMC) cells treated with TiDOL-C225-Alizarine.

FIG. 18 panel B clearly shows enhanced retention of TiDoL-C225 nanocomposites on the surface of EGFR+ colorectal cancerous HCT116 cells (panel B) while their retention (adsorption) in conditionally immortalized young adult mouse colonocyte (YAMC) cells that do not express EGFR (EGFR(-)) is negligible under the same conditions (panel C). Likewise, retention of TiDoL nanoconjugates in the absence of C225 antibody on HCT116 cells (EGFR(+)) was negligible as shown by faint red fluorescence of alizarin-modified TiDoL (panel A). Similar poor adherence of TiDoL-C225 was observed for EGFR(-) non-transformed fibroblast CT26 cells. These results suggest weak retention and poor activation of TiDoL-C225 within the healthy tissue compared to the one when TiDoL-C225 is integrated with cancerous EGFR(+) cells. Thus, FIG. 18 panel B reveals that the efficiency of TiDoL towards programmed cell death is significantly enhanced by functionalization with monoclonal antibody C225 that increases retention of the nanocomposites in tumor regions to mediate site selective light activity.

Figure 19:
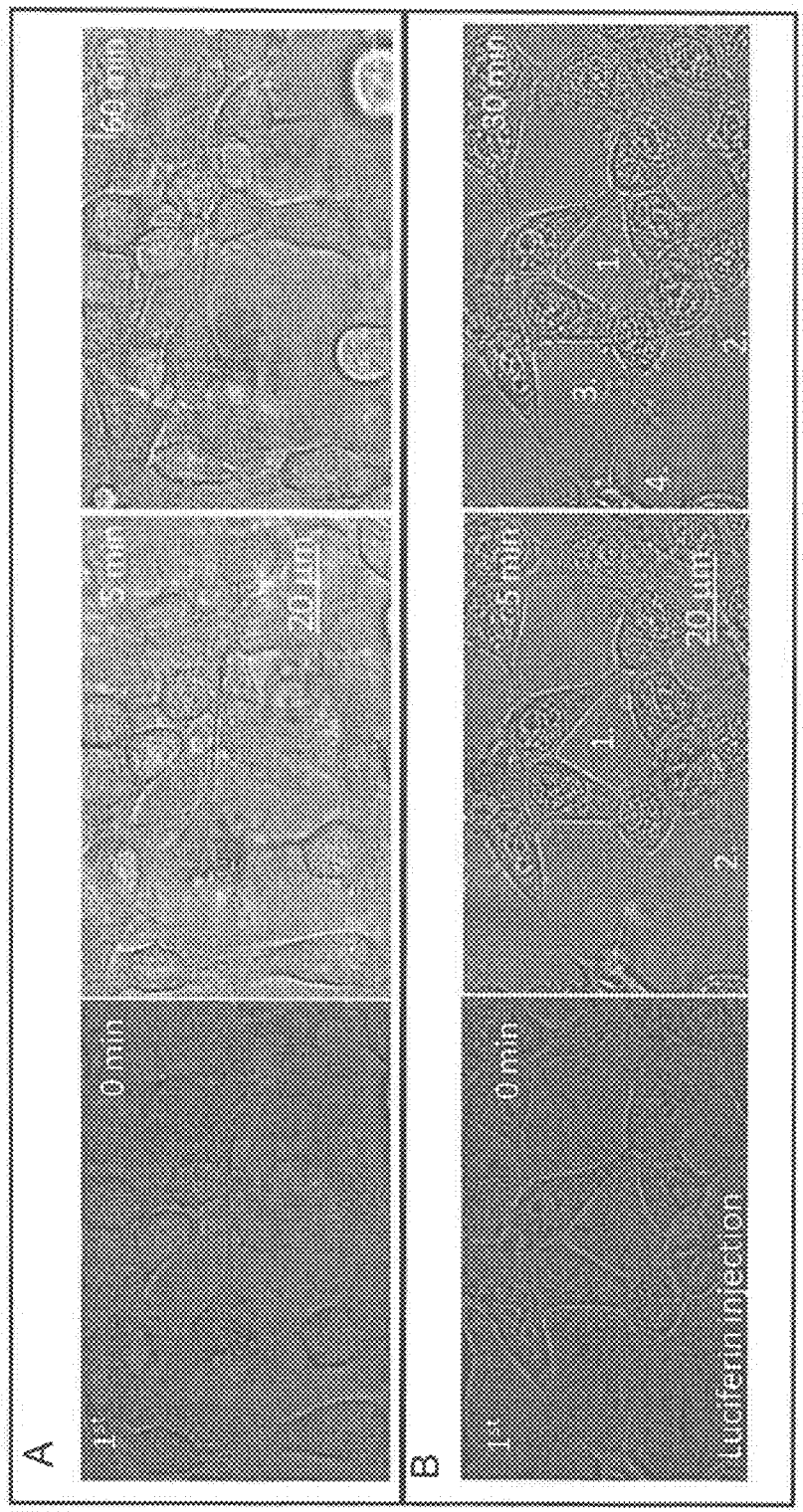
FIG. 19 panels A-B are time course optical images of morphological changes of YAMC cells (panel A) and HCT116 cells (panel B) treated with 150 nM TiDoL-C225 under the same conditions at 126× magnification. Cell budding was not observed in YAMC cells (Panel A), while in HCT116 cells (panel B) cell budding was observed to start at about 20 seconds after first luciferin injection.

FIG. 19 panel A shows time sequence of morphological changes associated with activation of TiDoL-C225 within conditionally immortalized YAMS cells (EGFR(-)) that show minor changes even 60 min after activation with luciferin. The composite does not produce cell budding in YAMS cells even after 3 doses of luciferin in the presence of ATP in the concentrations available in the healthy cell tissues. Similar results were obtained for CT26 EGFR-non-transformed fibroblast cells. Activation of TiDoL-C225 within HCT116 cells (EGFR+) resulted in a very fast cell budding, and as soon as 20 seconds after luciferin injection the cells show final stages of apoptotic death (FIG. 19 panel B).

Cell budding was accompanied with darkening of the nuclear membrane and enhancement of the image contrast as a result of chromatin rearrangement. Due to this rapid budding, the cells do not have time to go through the significant shrinking phase. However, the cells show strong and intact cytoplasmic membranes that extend to apoptotic bodies. Cells start to transfer their content to the apoptotic bodies 20 minutes after cell budding. These apoptotic bodies encapsulate the cell material, and can be recognized, engulfed, and ingested by macrophages in vivo enabling clearance of apoptotic cells in early stage of phagocytosis.

Effect of treatment with TiDoL was also investigated on 3D spheroids (three-dimensional tissue-like spheroid cell cultures which may serve as biological models of native tissues) so as to study metabolic processes in 3D tissue. The environment of cancerous cells in vitro differs greatly than in situ and in vivo, including biochemical factors and biological activity stemming from neighboring multidirectional attached cancerous cells. In addition only surface of 3D tissue is freely exposed to nanoparticles. Also hypoxic conditions that are prevalent deep in the cancer might prevent radical formation. 3D cell culture models provide a suitable analogue for in vivo studies so as to obtain better understanding of parameters that govern efficiency of nanoparticle therapies in real tumors.

The interaction of the TiDoL nanoparticles with different size of 3D cell cultures was studies to understand their diffusion and efficiency in these tissue models. 3D spheroids were grown using hanging drop method. 3D spheroids composed of HCT116 cells were incubated with TiDoL (or controls) and activated by two sequential aliquots of luciferin 30 min apart in a $CO_2$ incubator. Subsequently, spheroids were washed and stained using fluorescent wheat germ agglutinin (WGA, labeled with green Alexa Fluor® 488) and MITOTRACKER® Red.

Figure 20:
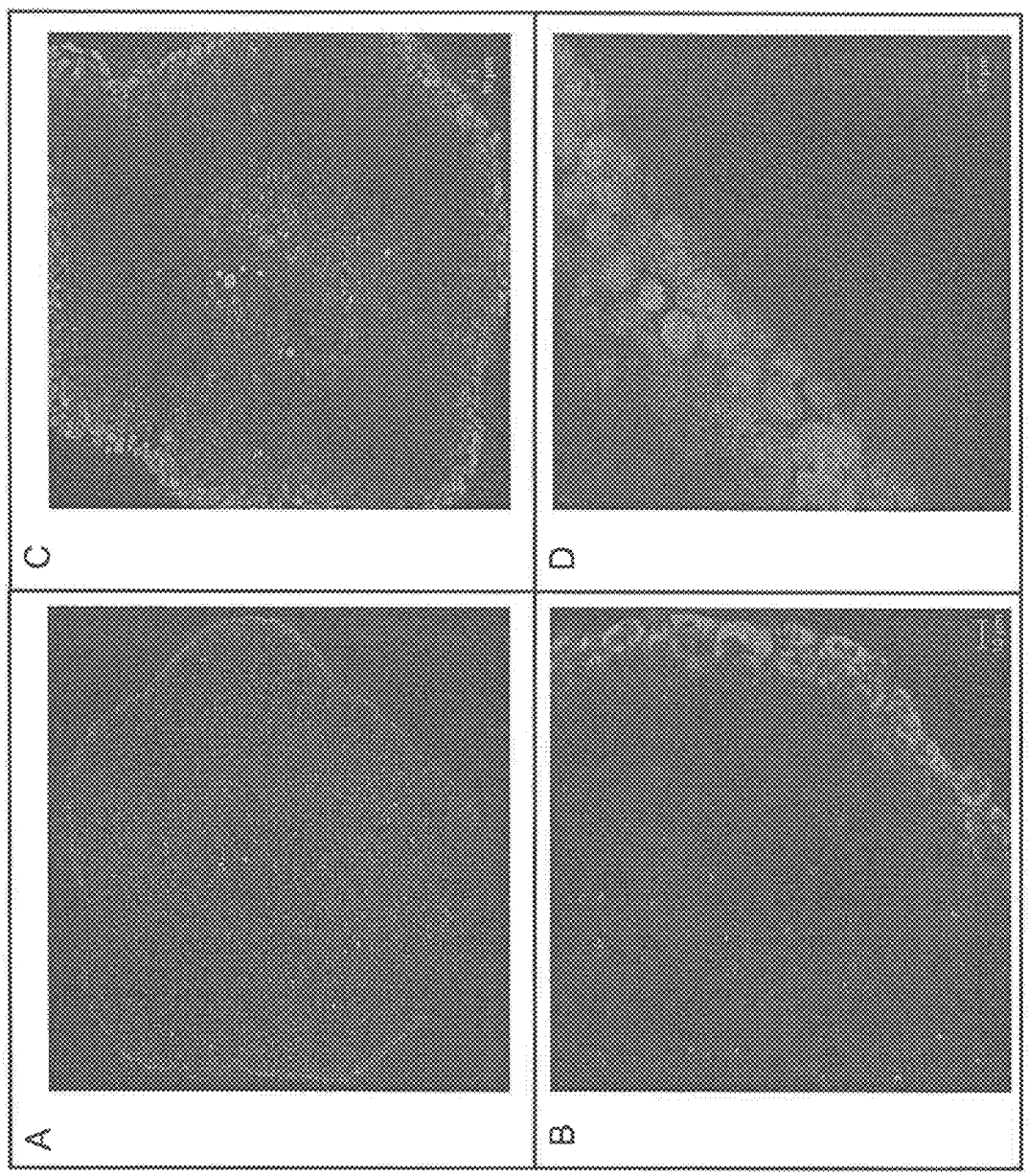
FIG. 20 panels A and B are optical fluorescence images of untreated HCT116 3D spheroids (tissue-like spheroid cultures which serve as biological models of native tissues) cells taken at 10× magnification (panel A) and 100× magnification (panel B), and FIG. 20 panels C and D are optical fluorescence images of HCT116 cells treated with TiDoL-C225 and luciferin taken at 10× magnification (panel C) and 100× magnification (panel D). Fluorescence was obtained by staining the cells with EGA and MITOTRACKER® excited at 488 nm and 561 nm, respectively.

FIG. 20 shows stained HCT116 cells incubated with TiDoL before (panels A and B) and after treatment with luciferin (panels C and D). The images show significant morphological changes after luciferin treatment. All the cells incubated with TiDoL only (panels A and B) remain unchanged and have well-defined cytoplasmic membranes, polarized mitochondria, and dark spherical regions in the place of the nucleus. After treatment with ATP and luciferin (panels C and D), the cells in the spheroid lose their morphological features. They shrink in size, the nuclear membrane becomes permeable and the nuclear region becomes barely identifiable. All of the contents of mitochondria and thiol containing proteins labeled with MITOTRACKER® become uniformly distributed throughout the cytoplasmic and nuclear regions and nuclear region is not any more identifiable suggesting cell death.

Figure 21:
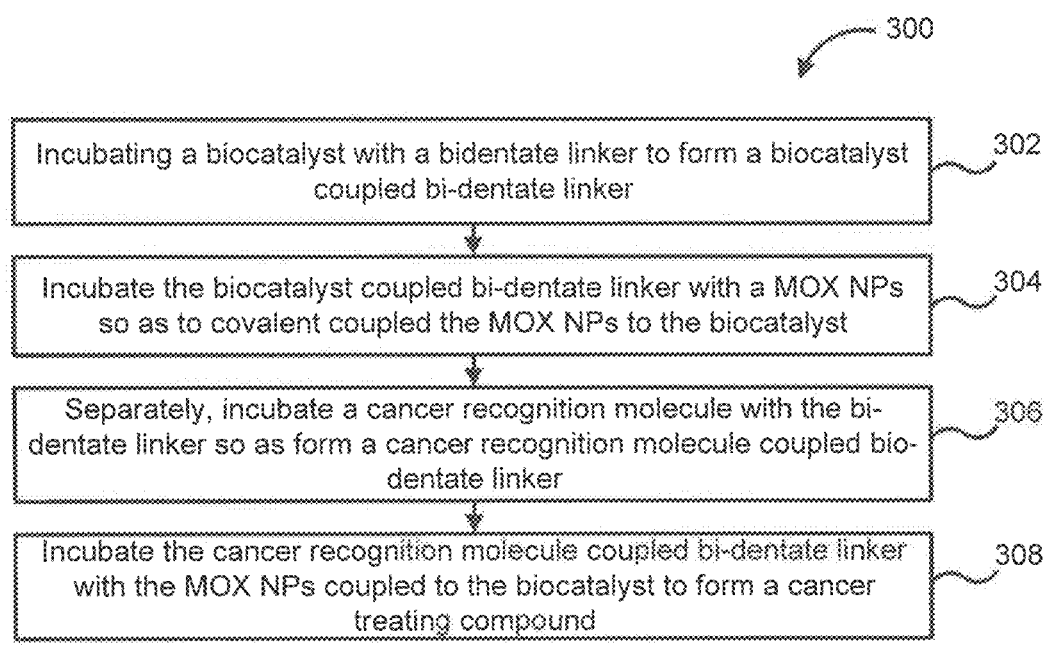
FIG. 21 is a schematic flow diagram of an example method of preparing a cancer treating composition, according to an embodiment.

FIG. 21 is a schematic flow diagram of an example method 300 of formulating a cancer treating composition. The method comprises incubating a biocatalyst with a bidentate linker in a buffer solution at a predetermined pH at 302. The incubating causes the biocatalyst to covalently couple to the bidentate linker, thereby forming a biocatalyst coupled bidentate linker. For example, luciferase is incubated with DOPAC in a buffer solutions (e.g., PBS) at a predetermined pH in the range of 6-7 inclusive of all ranges and values therebetween, as described with respect to FIG. 6.

The biocatalyst coupled bidentate linker is incubated with MOX NPs so as to covalently couple the MOX NPs to the bidentate linker, and thereby the biocatalyst at 304. The MOX NPs may include $TiO_2$, $Fe_xO_y$, $CeO_2$, $ZrO_2$, $V_xO_y$, $Mo_xO_y$, $Mn_xO_y$, NiO, AgO, $Cu_xO_y$ nanoparticles and/or any other suitable MOX NPs. In particular embodiments, the MOX NPs include $TiO_2$ NPs which may be covalently linked to the DOPAC linked luciferase so as to form TiDoL NPs, as described before herein.

A cancer recognition molecule is separately incubated with the bidentate linker so as to covalently couple the cancer recognition molecule to the bidentate linker, thereby forming a cancer recognition molecule coupled bidentate linker at 306. For example, the cancer recognition molecule C225 or any other cancer recognition molecule is incubated with DOPAC so as to covalently link the DOPAC or any other bidentate linker to the C225 antibody or any other cancer recognition molecule.

The cancer recognition molecule coupled bidentate linker is incubated with the MOX nanoparticles coupled to the biocatalyst at 308. The incubating causes the cancer recognition molecule to be also coupled to the MOX nanoparticles via the bidentate linker so as to form the cancer treating composition. For example, the DOPAC linked C225 antibody is incubated with the TiDoL NPs so as to covalently link the C225 to the TiDoL NPs, thereby forming TiDoL-C225 NPs which may be used to treat cancer. Each of the biocatalyst, the MOX nanoparticles and the cancer recognition molecule may be covalently coupled to the bidentate linker (e.g., DOPAC) using a carbodiimide (e.g., 1-ethyl-3-(-3-dimethylaminopropyl) carbodiimide (EDC) or N',N'-dicyclohexyl carbodiimide (DCC)) linking chemistry. For example, EDC-N-hydroxysuccinimide (NHS) chemistry may be used to cause the covalent coupling of the bidentate ligand (e.g., DOPAC) to the MOX NPs (e.g., $TiO_2$), the biocatalyst (e.g., luciferase) and the cancer recognition molecule (e.g., C225 antibody).

As described before, the cancer recognition molecule (e.g., C225) comprises a structure configured to selectively recognize a corresponding antigen on a surface of a cancer cell and bind to the antigen. The biocatalyst (e.g., luciferase) is structured to selectively catalyze the oxidation of a light emitting compound (e.g., luciferin) to produce photons, for example in the presence of ATP. The photons transform the MOX NPs into an excited state. The MOX NPs generate reactive oxygen species in the vicinity of the cancer cells in the excited state, which lyse the cancer cells or otherwise cause apoptosis in the cancer cells.

In some embodiments, a kit for treating cancer may comprise a first composition comprising a cancer recognition molecule linked TiDoL NPs and a first solution in a sealed container. The first solution may comprise a buffer (e.g., a PBS buffer, DMEM, HBSS, etc.) maintained at a suitable pH (e.g., in the range of 6-7 inclusive of all ranges and values therebetween), with the cancer recognition molecule linked TiDoL NPs suspended therein. In particular embodiments, the cancer recognition molecule may include C225 antibody or any other cancer recognition molecule. The concentration of the cancer recognition molecule linked TiDoL NPs in the buffer solution may be in the range of 10 nM to 10 micromolar (e.g., 10 nM, 20 nM, 30 nM, 40 nM, 50 nM, 60 nM, 70 nM, 80 nM, 90 nM, 100 nM, 150 nM, 200 nM, 300 nM, 400 nM, 500 nM, 600 nM, 700 nM, 800 nM, 900 nM, 1 micromolar, 2 micromolar, 3 micromolar, 4 micromolar, 5 micromolar, 6 micromolar, 7 micromolar, 8 micromolar, 9 micromolar or 10 micromolar, inclusive of all ranges and values therebetween). The first composition may be administered first to a subject (e.g., a cancer patient).

The kit also includes a second composition comprising D-luciferin. In some embodiments, the second composition may be in the form of a powder or crystals which are dissolved in a suitable solution (e.g., a PBS buffer, Dulbecco's modified eagle's medium (DMEM) buffer, DMEM with 10% fetal bovine serum (FBS) or any other suitable buffer) to form a 100-200 micrograms per milliliter solution of D-luciferin, inclusive. In other embodiments, the second composition may include a buffer solution of D-luciferin at a concentration of 100-200 micrograms per milliliter solution of D-luciferin, inclusive. The second composition may be delivered to the subject (e.g., injected into the subject) several times after the first composition has been delivered to the subject.

For example, the first composition may be delivered first to the subject, and after a predetermined incubating time within the subject, a first bolus of the second composition may be delivered to the subject. A second bolus of the second composition may be delivered to the subject after a second predetermined time, and so on, until a desired dose of the second composition has been delivered to the subject. The combination of the first composition and the second composition may selectively lyse or induce apoptosis in cancer cells present in any portion of a body of the subject as previously described herein.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

As used herein, the terms "about" and "approximately" generally mean plus or minus 10% of the stated value. For example, about 0.5 would include 0.45 and 0.55, about 10 would include 9 to 11, about 1000 would include 900 to 1100.

The terms "coupled," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Additionally, it should be understood that features from one embodiment disclosed herein may be combined with features of other embodiments disclosed herein as one of ordinary skill in the art would understand. Other substitutions, modifications, changes and omissions may also be made in the design, operating conditions and arrangement of the various exemplary embodiments without departing from the scope of the present invention.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings and tables in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A nanostructure, comprising:
a metal oxide (MOX) nanoparticle;
a first bidentate ligand and a second bidentate ligand disposed on a surface of the MOX nanoparticle;
a cancer recognition molecule covalently coupled to the surface of the MOX nanoparticle via the first bidentate ligand; and
a luciferase coupled to the surface of the MOX nanoparticle via the second bidentate ligand,
wherein, the cancer recognition molecule comprises a structure configured to selectively recognize a corresponding antigen on a surface of a cancer cell and bind to the antigen, and wherein the luciferase is structured to selectively catalyze the oxidation of a light emitting compound to produce photons, the photons transforming the MOX nanoparticles into an excited state, the MOX nanoparticles generating reactive oxygen species in the vicinity of the cancer cells in the excited state, the reactive oxygen species configured to at least one of lyse the cancer cell or cause apoptosis in the cancer cell.

2. The nanostructure of claim 1, wherein the MOX nanoparticles include at least one of $TiO_2$, $Fe_xO_y$, $CeO_2$, $ZrO_2$, $V_xO_y$, $Mo_xO_y$, $Mn_xO_y$, NiO, AgO and $Cu_xO_y$ nanoparticles.

3. The nanostructure of claim 2, wherein the MOX nanoparticles include a hybrid metal/MOX nanoparticle.

4. The nanostructure of claim 3, wherein the metal included in the hybrid metal/MOX nanoparticle includes at least one of Au and Ag.

5. The nanostructure of claim 3, wherein the hybrid metal/MOX nanoparticles include at least one of a core-shell and dumbbell shaped nanoparticles.

6. The nanostructure of claim 2, wherein the MOX nanoparticles include $TiO_2$ nanoparticles.

7. The nanostructure of claim 1, wherein each of the first bidentate ligand and the second bidentate ligand includes 3,4-dihydroxyphenylacetic acid (DOPAC).

8. The nanostructure of claim 1, wherein the cancer recognition molecule comprises C225 antibody or IL13.

9. A method of treating cancer using a plurality of nanostructures comprising a MOX nanoparticle having a cancer recognition molecule and a luciferase coupled to a surface of the MOX nanoparticle via a first bidentate ligand and a second bidentate ligand, respectively, the method comprising:
injecting the plurality of nanostructures into a patient having cancer cells, the plurality of nanostructures injected at a cancer site in a body of the patient where the cancer cells are located, the cancer cells producing adenosine triphosphate (ATP);
incubating the plurality of nanostructures at the cancer site for a first predetermined time, wherein the plurality of nanostructures selectively bind to the cancer cells via the cancer recognition molecule;
injecting a light emitting compound into a blood stream of the patient;
incubating the light emitting compound in the blood stream of the patient for a second predetermined time, the incubating allowing the light emitting compound to be transported to the nanostructures selectively bound on the cancer cells,
wherein the luciferase catalyzes oxidation of the light emitting compound in the presence of the ATP to produce photons in proximity of the cancer cells,
wherein the MOX nanoparticles are excited via the photons to generate reactive oxygen species in proximity of the cancer cells, and
wherein the reactive oxygen species interact with the cancer cells to cause at least one of lysis or apoptosis in the cancer cells.

10. The method of claim 9, wherein the MOX nanoparticles include $TiO_2$.

11. The method of claim 9, wherein each of the first bidentate ligand and the second bidentate ligand includes DOPAC.

12. The method in claim 9, wherein the cancer recognition molecule is monoclonal antibody C225 or IL13.

13. The method of claim 10, wherein the cancer cells include at least one of colorectal cancer cells, pancreatic cancer cells, liver cancer cells, prostate cancer cells, stomach cancer cells, throat cancer cells, brain cancer cells, melanoma, A172 human glioblastoma, astrocytoma, IL-13Ra2-positive U251 MG cells and IL-13Ra2-positive cancer cells.

14. The method of claim 9, further comprising:
exposing the MOX nanoparticle to a magnetic field, the magnetic field enhancing the generation of the reactive oxygen species and increasing an efficiency of the lysing of the cancer cells.

15. A method of formulating a cancer treating composition, comprising:
incubating a luciferase with a first bidentate ligand in a buffer solution at a predetermined pH, the incubating causing the luciferase to covalently couple to the first bidentate ligand, thereby forming a luciferase coupled first bidentate ligand;
incubating the luciferase coupled first bidentate ligand with metal oxide (MOX) nanoparticles so as to covalently couple the MOX nanoparticles to the first bidentate ligand and, thereby the luciferase; and
separately, incubating a cancer recognition molecule with a second bidentate ligand so as to covalently couple the cancer recognition molecule to the second bidentate ligand, thereby forming a cancer recognition molecule coupled second bidentate ligand; and
incubating the cancer recognition molecule coupled second bidentate ligand with the MOX nanoparticles coupled to the luciferase, the incubating causing the cancer recognition molecule to be also coupled to the MOX nanoparticles via the second bidentate ligand so as to form the cancer treating composition,
wherein, the cancer recognition molecule comprises a structure configured to selectively recognize a corresponding antigen on a surface of a cancer cell and bind to the antigen, and wherein the luciferase is structured to selectively catalyze the oxidation of a light emitting compound to produce photons, the photons transforming the MOX nanoparticles into an excited state, the MOX nanoparticles configured to generate reactive oxygen species in the vicinity of the cancer cells in the excited state, the reactive oxygen species lysing or causing apoptosis in the cancer cell.

16. The method of formulating a cancer treating composition of claim 15, wherein the MOX nanoparticles include at least one of $TiO_2$, $Fe_xO_y$, $CeO_2$, $ZrO_2$, $V_xO_y$, $Mo_xO_y$, $Mn_xO_y$, NiO, AgO and $Cu_xO_y$ nanoparticles.

17. The method of formulating a cancer treating composition of claim 15, wherein each of the first bidentate ligand and the second bidentate ligand include 3,4-dihydroxyphenylacetic acid (DOPAC), and wherein each of the luciferase, the MOX nanoparticles and the cancer recognition molecule are covalently coupled to the DOPAC using a carbodiimide linking chemistry.

* * * * *